(12) United States Patent
Takahashi et al.

(10) Patent No.: US 11,193,107 B2
(45) Date of Patent: Dec. 7, 2021

(54) SUBSTRATE FOR SUPPORTING CELLS AND METHOD FOR PRODUCING SAME

(71) Applicants: EBARA JITSUGYO CO., LTD., Tokyo (JP); KEIO UNIVERSITY, Tokyo (JP)

(72) Inventors: Shuichi Takahashi, Kawasaki (JP); Michio Ohira, Kawasaki (JP); Hideo Nakata, Kawasaki (JP); Shogo Miyata, Yokohama (JP); Shugo Tohyama, Tokyo (JP); Jun Fujita, Tokyo (JP); Keiichi Fukuda, Tokyo (JP)

(73) Assignees: Ebara Jitsugyo Co., Ltd., Tokyo (JP); Keio University, Tokyo (JP)

( * ) Notice: Subject to any disclaimer, the term of this patent is extended or adjusted under 35 U.S.C. 154(b) by 935 days.

(21) Appl. No.: 15/552,973

(22) PCT Filed: Feb. 24, 2016

(86) PCT No.: PCT/JP2016/000981
§ 371 (c)(1),
(2) Date: Nov. 30, 2017

(87) PCT Pub. No.: WO2016/136251
PCT Pub. Date: Sep. 1, 2016

(65) Prior Publication Data
US 2018/0201898 A1 Jul. 19, 2018

(30) Foreign Application Priority Data

Feb. 25, 2015 (JP) .............................. JP2015-035439

(51) Int. Cl.
| | | |
|---|---|---|
| *A61L 29/16* | (2006.01) | |
| *B29C 71/04* | (2006.01) | |
| *C12N 5/00* | (2006.01) | |
| *C12N 5/10* | (2006.01) | |
| *C12M 1/12* | (2006.01) | |
| *C12N 5/0735* | (2010.01) | |
| *C12N 5/077* | (2010.01) | |

(52) U.S. Cl.
CPC ........... *C12N 5/0068* (2013.01); *C12M 25/02* (2013.01); *C12N 5/0606* (2013.01); *C12N 5/0656* (2013.01); *C12N 5/10* (2013.01)

(58) Field of Classification Search
None
See application file for complete search history.

(56) References Cited

U.S. PATENT DOCUMENTS

| | | | |
|---|---|---|---|
| 5,023,026 A | 6/1991 | Yoshida et al. | |
| 2010/0273259 A1* | 10/2010 | Saha | C12N 5/0068 435/377 |
| 2014/0087465 A1 | 3/2014 | Yoshikawa et al. | |
| 2019/0085137 A1* | 3/2019 | Satoh | C08J 3/12 |

FOREIGN PATENT DOCUMENTS

| | | |
|---|---|---|
| JP | 63-152973 A | 6/1988 |
| JP | 06-098756 A | 4/1994 |
| JP | 2004-254516 A | 9/2004 |
| JP | 2007-267673 A | 10/2007 |
| JP | 2009-017809 A | 1/2009 |
| JP | 2010-068755 A | 4/2010 |
| JP | 2011-510655 A | 4/2011 |
| JP | 2012-175983 A | 9/2012 |
| JP | 2012-527896 A | 11/2012 |
| WO | WO 2009/008547 A1 | 1/2009 |
| WO | WO 2009/099555 A2 | 8/2009 |
| WO | WO 2010/124091 A1 | 10/2010 |
| WO | WO 2010/138486 A1 | 12/2010 |
| WO | WO 2012/144624 A1 | 10/2012 |

OTHER PUBLICATIONS

"Biomaterials and biodevices for alternative methods to animal testing," supervised by Yasuyuki Sakai and Eiichi Mintani, CMC Publishing Co., Ltd., pp. 133-134 (2014).
European search report for Application No. 16755001.1 dated Sep. 19, 2018 in 16 pages.
Mahlstedt M. M et al., "Maintenance of pluripotency in human embryonic stem cells cultured on a synthetic substrate in conditioned medium", Biotechnology and Bioengineering, Wiley, US 105(1) (2010): pp. 130-140.
R. K. Wells, "Surface engineering of polymers", Ph. D. Thesis, Dept. of Chem. Univ. of Duham. UK (1994): pp. 1-237.
S Robertson et al., "Time-of-flight secondary ion mass spectrometry (TOF-SIMS) for high-throughput characterization of biosurfaces", Applied Surface Science 203-204 (2003): pp. 855-858.
V. D. Wel H et al., "Surface modification of polycarbonate by u.v. light as studied by TOF-SIMS", Polymer, Elsevier Science Puiblishers B.V, GB, 10 (1) (1993): pp. 2065-2071.
Yang J et al., "Polymer surface functionalities that control human embryoid body cell adhesion revealed by high throughput surface characterization of combinatorial material microarrays," Biomaterials, Elsevier Science Puiblishers B.V, GB, 31 (34) (2010): pp. 8827-8838.
International Search Report for International Application No. PCT/JP2016/000981, dated May 24, 2016.
Formosa et al., "UV-$O_3$-treated and protein-coated polymer surfaces facilitate endothelial cell adhesion and proliferation mediated by the PKCα/ERK/cPLA$_2$ pathway," *Microvascular Research*, vol. 75, pp. 330-342 (2008).

(Continued)

Primary Examiner — Maria G Leavitt
(74) Attorney, Agent, or Firm — Knobbe, Martens, Olson & Bear, LLP

(57) ABSTRACT

The invention provides a method for producing a substrate for supporting cells, including a humidification step of humidifying the periphery of a non-fluorine resin based substrate, and a UV irradiation step of irradiating the substrate with UV in an oxygen and/or ozone containing atmosphere during and/or after the humidification step. The invention also provides a substrate for supporting cells, which is a non-fluorine resin based substrate. The substrate has a cell supporting surface for supporting cells, containing a component capable of generating $C_7H_5O^+$ molecules by beam irradiation of a time-of-flight secondary ion mass spectrometer, such that cells are supported on the cell-supporting surface.

15 Claims, 17 Drawing Sheets

(56) References Cited

OTHER PUBLICATIONS

Mitchell et al., "Cellular attachment and spatial control of cells using micro-patterned ultra-violet/Ozone treatment in serum enriched media," *Biomaterials*, vol. 25, pp. 4079-4086 (2004).

Poulsson et al., "Attachment of Human Primary Osteoblast Cells to Modified Polyethylene Surfaces," *Langmuir*, vol. 25, pp. 3718-3727 (2009).

Tamada et al., "Fibroblast growth on polymer surfaces and biosynthesis of collagen," *Journal of Biomedical Materials Research*, vol. 28, pp. 783-789 (1994).

Teare et al., "Cellular Attachment to Ultraviolet Ozone Modified Polystyrene Surfaces," *Langmuir*, vol. 16, pp. 2818-2824 (2000).

Williams et al., "Computerised Measurement of Contact Angles" Galvanotechnik (2010) 101: 2502-2512.

Office Action, dated Jun. 13, 2017, in Japanese Patent Application No. JP 2017-501942.

\* cited by examiner miPSCs cultured
on feeder layer miPSCs cultured
on non-treated dish
(feeder- and gelatin-free)

miPSCs cultured on
ozone/UV (1min)-modified
substrate
(feeder- and gelatin-free)

miPSCs cultured on
ozone/UV (3min)-modified
substrate
(feeder- and gelatin-free)

miPSCs cultured on
ozone/UV (10min)-modified
substrate
(feeder- and gelatin-free)

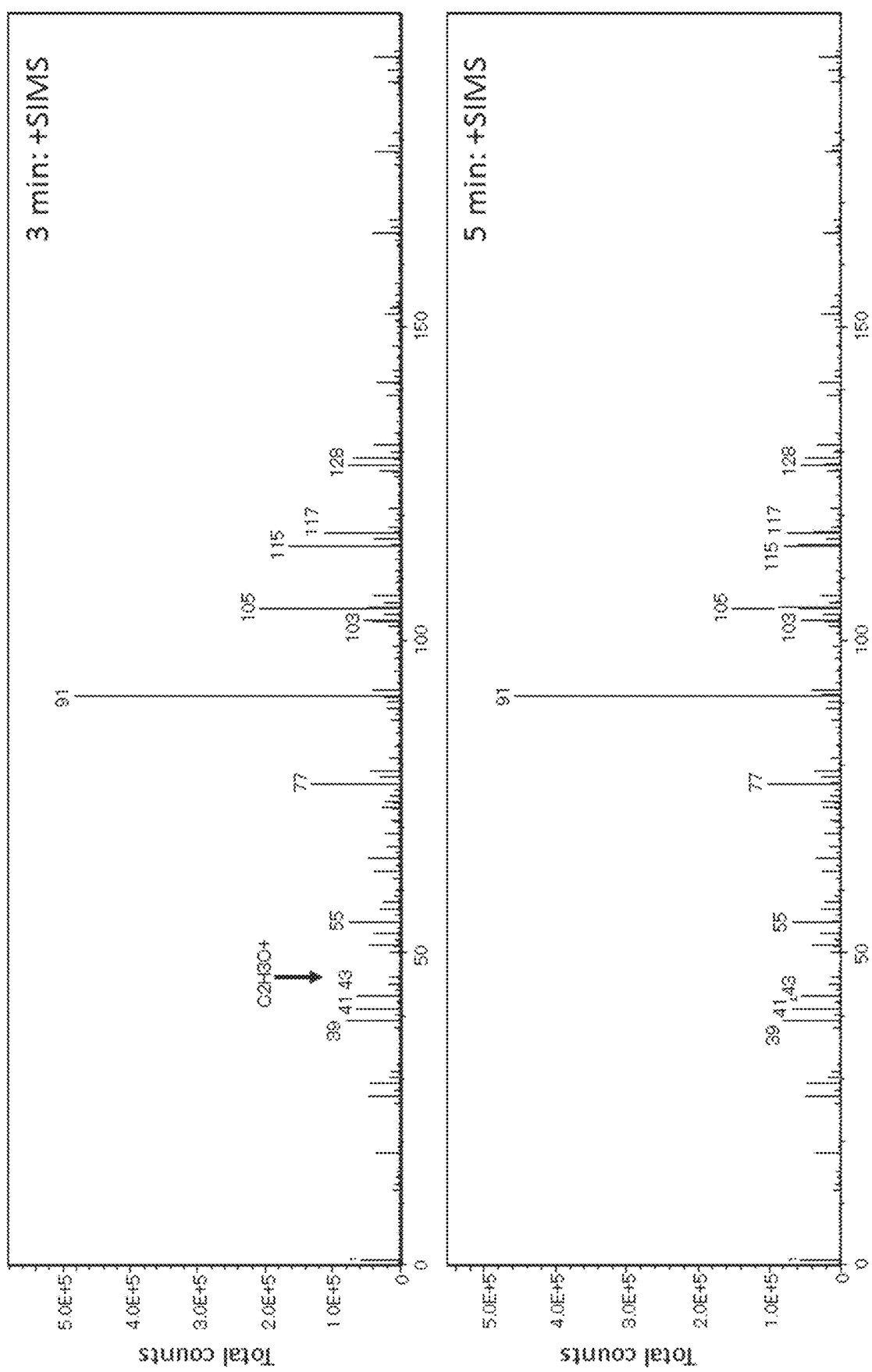

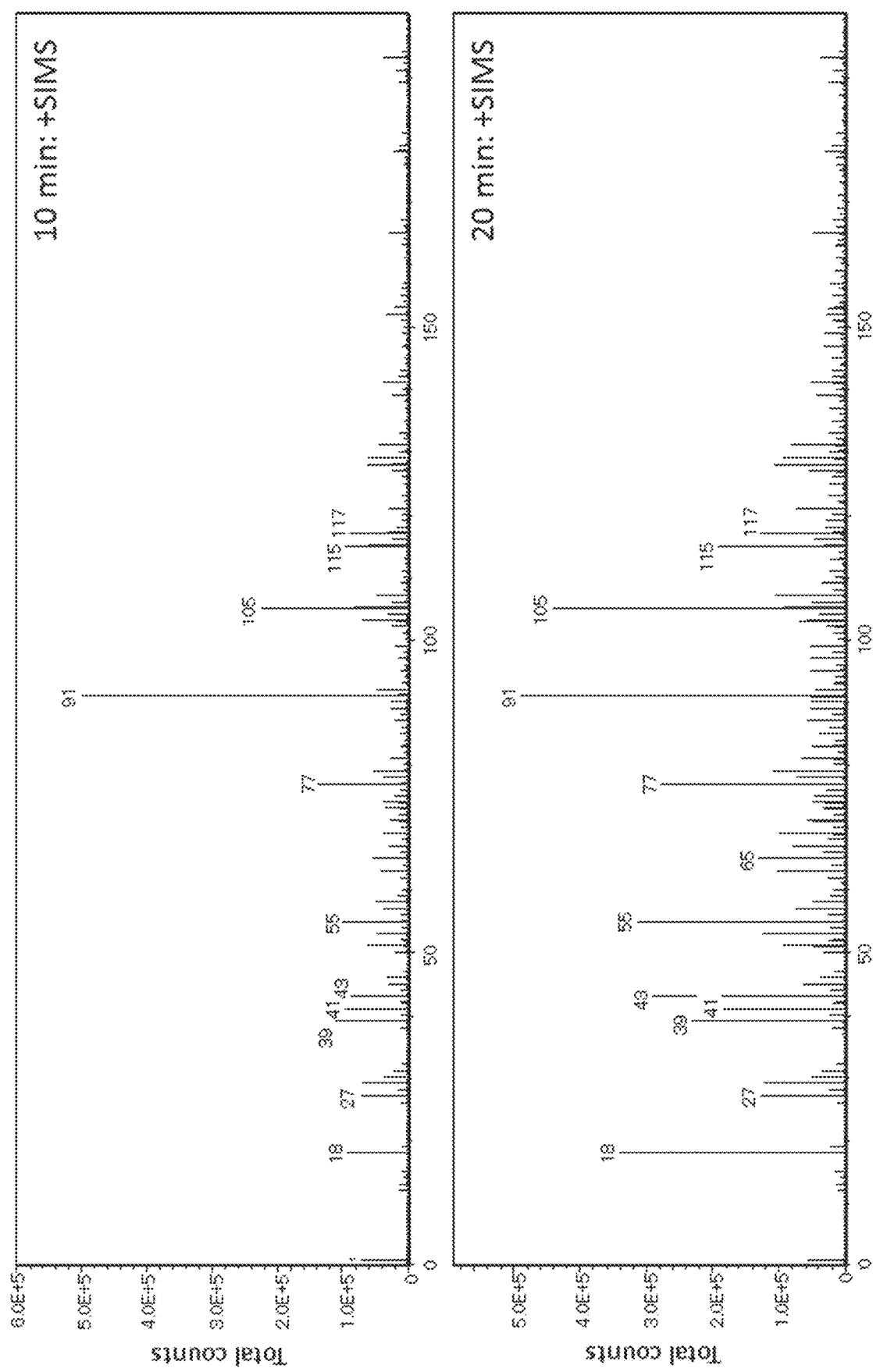

SUBSTRATE FOR SUPPORTING CELLS AND METHOD FOR PRODUCING SAME

CROSS REFERENCE

This application claims the priority based on Japanese Patent Application No. 2015-035439 filed on 25 Feb. 2015 in Japan, the content of which is incorporated herein in its entirety by reference. Also, the contents of all patents, patent applications and literatures are incorporated herein in their entirety by reference.

TECHNICAL FIELD

The present invention relates to a substrate for supporting cells having a surface suitable for supporting, attaching, preserving, culturing and/or proliferating cells, and a method for producing the substrate.

BACKGROUND ART

It is known that adherent cells barely adhere to hydrophobic surface and highly hydrophilic surface, but adhere to adequate hydrophilic surface on which cells have extended form. Particularly, it has been known that cells well adhere to the surface with medium degree of wettability having a water contact angle of 40 to 70° (Non Patent Literature 1) or 60 to 80° (Non Patent Literature 2). Thus, means for obtaining such an adequate hydrophilic surface being superior in adhesion and proliferation of adherent cells have been developed. Until now, following methods have been reported as a method for imparting hydrophilicity to a polymer-material surface: an atmospheric-pressure plasma treatments (Patent Literature 2) such as a corona discharge treatment (Patent Literature 1); and chemical modifications such as grafting a polymer chain containing a hydrophilic skeleton (Patent Literature 3), a substrate controlled to have a contact angle of about 10 to 30° by binding an aminopropyl ethylene maleic anhydride onto the surface (Patent Literature 4), and a method of exposing a hydrophilic group of an amphiphilic substance on a surface (Patent Literature 5). As a method for controlling hydrophilicity on surface, following methods have been reported: a method that once prepares highly hydrophilic surface and then reduces the hydrophilicity by an oxidation treatment and/or a decomposition treatment; and a method of binding a hydrophilic molecule to a surface via a linker wherein hydrophilicity is controlled by changing the density of the linker (Patent Literature 6). Among these methods, the physical methods such as a corona discharge treatment and an atmospheric pressure plasma treatment are particularly simple, and thus principally used for modifying a hydrophilic surface for cell culture.

In such a hydrophilic surface, it is considered that a group having an oxygen atom such as a hydroxyl group, a carbonyl group and a carboxy group, mainly contributes to hydrophilicity. However, oxygen atoms introduced by corona discharge are rapidly removed, which leads easily deteriorating of surface. Moreover, the corona discharge treatment is considered to have a limitation in imparting hydrophilicity to a surface because it can provide only 20% surface oxygen onto a substrate. Plasma discharge can attain a higher oxygen level than corona discharge, but a substrate needs to be treated in a vacuum and a treatment process was complicated. In addition, the plasma treatment has a problem of easily damaging a surface.

As another approach for imparting hydrophilicity to a polymer material surface, a method of applying ultraviolet laser (Patent Literature 4) and a method of applying a ultraviolet ray of a wavelength capable of generating ozone, to a fluororesin substrate and the like (Non Patent Literatures 3 and 4) have been reported. These reports also describe that the surface oxygen atom ratio is desirably middle for cell proliferation (Non Patent Literature 4). Other attempt to improve the ozone/UV methods includes combination of ozone/UV treatment with a biomaterial (Non Patent Literature 5), and introduction of oxygen atoms into a super-high-molecular polyethylene (Non Patent Literature 6).

Particularly, in using a hydrophilic surface as a substrate for culturing undifferentiated cells, it is more difficult to culture undifferentiated cells including stem cells, and specific environments have been required such as feeder cells, cytokines including LIF, or coating with an extracellular matrix protein such as Matrigel (registered trade mark) or collagen. However, these techniques all depend upon bio-derived materials, which may cause problems of low stability, variance in results due to lot difference, possibility of contamination, and short preservation life.

Further attempts to produce a stable surface for cell culture which is able to culture undifferentiated cells including stem cells by chemical modification have been reported. For example, a method of forming swellable (metha) acrylate layer on the cell culture surface has been proposed to solve these problems (Patent Literature 7).

CITATION LIST

Patent Literature

Patent Literature 1: Japanese Patent Laid-Open No. H6-98756

Patent Literature 2: International Publication No. WO2012/144624

Patent Literature 3: Japanese Patent Laid-Open No. 2009-17809

Patent Literature 4: National Publication of International Patent Application No. 2012-527896

Patent Literature 5: Japanese Patent Laid-Open No. 2012-175983

Patent Literature 6: National Publication of International Patent Application No. 2011-510655

Patent Literature 7: Japanese Patent Laid-Open No. 2010-68755

Non Patent Literature

Non Patent Literature 1: "Biomaterials and biodevices for alternative methods to animal testing" supervised by Yasuyuki Sakai and Eiichi Tamiya, CMC Publishing Co., Ltd., 2014, pages 133-134

Non Patent Literature 2: Yasushi Tamada et al., Journal of Biomedical Materials Research; 28: 783-789 (1994)

Non Patent Literature 3: D. O. H. Teare et al., Kanbmuir; 16: 2818-2824 (2000)

Non Patent Literature 4: S. A. Mitchell et al., Biomaterials; 25: 4079-4086 (2004)

Non Patent Literature 5: Fabio Formosa et al., Microvascular Research; 75: 330-342 (2008)

Non Patent Literature 6: Alexandra H. C. Poulsson et al., Langmuir; 25: 3718-3727 (2009)

SUMMARY OF INVENTION

Technical Problem

The present invention was made in view of the above circumstances. An object of the present invention is to provide a simpler method for modifying a surface for supporting and culturing cells, which stably imparts hydrophilicity that is suitable for cell adhesion. Another object of the present invention is to provide a substrate for supporting cells, capable of supporting or culturing stem cells without a specific environment such as feeder cells or coating with an extracellular matrix protein such as Matrigel (registered trade mark) (Corning Incorporated, New York State, USA) or collagen.

Solution to Problem

The inventors applied various treatments to a surface of a resin substrate, investigated the relationship between the treatment and cell proliferation, and finally found that applying UV in a humidified oxygen and/or ozone atmosphere generates a surface suitable for cell adhesion and cell proliferation and completed the invention. Furthermore, the inventors found that the stem cells cultured on this surface can maintain its function and properties without differentiating under the condition that neither feeder cells nor a coating with an extracellular matrix protein such as Matrigel (registered trade mark) (Corning Incorporated, New York State, USA, the same applies below) or collagen exists, and completed the invention.

The invention includes the following:

[1] A non-fluorine resin based substrate for supporting cells, comprising a cell supporting surface, wherein the surface contains a component capable of generating $C_7H_5O^+$ molecules by beam irradiation of a time-of-flight secondary ion mass spectrometer, and cells are to be supported on the surface.

[2] The substrate for supporting cells of [1], wherein the ratio of the $C_7H_5O^+$ molecules to all molecules generated by beam irradiation of the time-of-flight secondary ion mass spectrometer on the cell supporting surface, is 0.015 or more.

[3] The substrate for supporting cells of [1] or [2], wherein the proportion of a ratio of the C2H3O+ molecules to all molecules to the ratio of the C7H5O+ molecules to all molecules, which are generated by beam irradiation of the time-of-flight secondary ion mass spectrometer on the cell supporting surface, is 0.485 or less.

[4] The substrate for supporting cells of any one of [1] to [3], wherein the cell supporting surface was caused a chemical shift of C—C bond and/or C—H bond.

[5] The substrate for supporting cells of any one of [1] to [4], wherein the cell supporting surface has substantially no carboxy groups.

[6] The substrate for supporting cells of any one of [1] to [5], the cell supporting surface has a water contact angle of 40 to 70°.

[7] The substrate for supporting cells of any one of [1] to [6], wherein the cell supporting surface enables stem cells to adhere or proliferate on the surface with maintaining an undifferentiated state in the absence of feeder cells.

[8] The substrate for supporting cells of any one of [1] to [7], wherein the cell supporting surface enables stem cells to adhere or proliferate on the surface under existence of Matrigel (registered trade mark) at 0.2 fold concentration of that required for adhesion of the stem cells onto a non-treated surface of the non-fluorine resin based substrate.

[9] The substrate for supporting cells of any one of [1] to [8], wherein the cell supporting surface enables stem cells to adhere or proliferate under existence of laminin at 0.2 fold concentration of that required for adhesion of the stem cells onto a non-treated surface of the non-fluorine resin based substrate.

[10] The substrate for supporting cells of [8] or [9], wherein the stem cells are mouse iPS cells or human iPS cells.

[11] The substrate for supporting cells of any one of [1] to [10], wherein the non-fluorine resin is at least one resin selected from the group consisting of a polyethylene, an acrylic resin, an ABS resin, a polyethylene terephthalate, a polypropylene, a polycarbonate and a polystyrene.

[12] The substrate for supporting cells of [11], wherein the non-fluorine resin is a polystyrene.

[13] The substrate for supporting cells of any one of [1] to [12], wherein the substrate is an adherent cell culturing container.

[14] The substrate for supporting cells of [13], wherein the adherent cell culturing container is a dish for adherent cell culture.

[15] A method for producing a substrate for supporting cells having a cell supporting surface, comprising
a humidification step of humidifying the periphery of a non-fluorine resin based substrate, and
a UV irradiation step of irradiating UV to the cell supporting surface of the substrate under an oxygen and/or ozone atmosphere during and/or after the humidification step.

[16] The method for producing a substrate for supporting cells of [15], wherein the non-fluorine resin is at least one resin selected from the group consisting of a polyethylene, an acrylic resin, an ABS resin, a polyethylene terephthalate, a polypropylene, a polycarbonate and a polystyrene.

[17] The method for producing a substrate for supporting cells of [16], wherein the non-fluorine resin is a polystyrene.

[18] The method for producing a substrate for supporting cells of any one of [15] to [17], wherein the UV irradiation is performed by applying UV beams with wavelength of 184.9 nm and 253.7 nm in average.

[19] The method for producing a substrate for supporting cells of any one of [15] to [18], wherein the UV irradiation is performed until a water contact angle of a surface of the non-fluorine resin becomes between 40 and 700.

[20] The method for producing a substrate for supporting cells of any one of [15] to [19], wherein the UV irradiation is performed for 1 to 3 minutes.

[21] The production method of any one of [15] to [20], wherein UV having wavelength of 184.9 and 253.7 nm are irradiated from two 6 W ozone generation lamps.

[22] The production method of any one of [15] to [21], wherein the distance from the UV lamps to the substrate is 3 to 5 cm.

[23] A substrate for supporting cells produced by the method of any one of [15] to [22].

[24] A method for culturing adherent cells, comprising culturing cells on the cell supporting surface of the substrate for supporting cells of any one of [1] to [14] and [23].

[25] The method for culturing of [24], wherein the adherent cells are stem cells.

[26] The method for culturing of [25], wherein the stem cells are mouse iPS cells or human iPS cells.

[27] The method for culturing of [25] or [26], wherein cells are cultured in an absence of feeder cells.

[28] The method for culturing of any one of [25] to [27], wherein cells are cultured in the presence of Matrigel (registered trade mark) at 0.2 fold concentration of that required for stem cells to adhere onto a non-treated surface of the non-fluorine resin based substrate.

[29] The method for culturing of any one of [25] to [28], wherein cells are cultured in the presence of laminin at 0.5 fold concentration of that required for stem cells to adhere onto a non-treated surface of the non-fluorine resin based substrate.

[30] A method for preserving adherent cells, comprising preserving cells cultured by the method for culturing of any one of [24] to [29].

According to another embodiment of the invention, the following inventions may be included.

(1) A non-fluorine resin based substrate for supporting cells, wherein at least part of a surface was caused a chemical shift of C—C bond and/or C—H bond, and cells are to be supported on the surface.

(2) The substrate for supporting cells of (1), wherein the cell supporting surface has substantially no carboxy groups.

(3) The substrate for supporting cells of (1) or (2), wherein the cell supporting surface enables stem cells to support or proliferate in an undifferentiated state in the absence of feeder cells (scaffold cells) and coating with an extracellular matrix protein.

(4) A method for producing a substrate for supporting cells having a cell supporting surface, comprising
a humidification step of humidifying the periphery of a non-fluorine resin based substrate, and
a UV irradiation step of irradiating the cell supporting surface of the substrate with UV under an oxygen and/or ozone atmosphere during and/or after the humidification step.

(5) The method for producing a substrate for supporting cells of (4), wherein the non-fluorine resin is at least one resin selected from the group consisting of a polyethylene, an acrylic resin, an ABS resin, a polyethylene terephthalate, a polypropylene, a polycarbonate and a polystyrene.

(6) The method for producing a substrate for supporting cells of (4) or (5), wherein the UV irradiation is performed by applying UV beams having an average wavelength of 184.9 nm and 253.7 nm.

(7) The method for producing a substrate for supporting cells of any one of (4) to (6), wherein the UV irradiation is performed until the water contact angle with the non-fluorine resin surface becomes between 40 and 70°.

(8) The production method of any one of (4) to (7), wherein the cell supporting surface can support stem cells or enables stem cells to proliferate on the surface, with maintaining an undifferentiated state, in the absence of feeder cells (scaffold cells) and coating with an extracellular matrix protein.

(9) A cell-culture container for adherent cells having a substrate for supporting cells of any one of (1) to (3) or a substrate for supporting cells produced by the production method of any one of (4) to (8).

(10) The cell-culture container of (9), which at least has a part of surface that can support stem cells or can enable stem cells to proliferate, with maintaining an undifferentiation state, in the absence of feeder cells (scaffold cells) and coating with an extracellular matrix protein.

(11) A culture method for culturing adherent cells, comprising culturing the cells on the cell supporting surface of the cell-culture container of (9) or (10).

(12) The culture method of (11), wherein the adherent cells are stem cells.

In the specification, the "substrate for supporting cells" is a substrate, which is to be used for supporting cells on the surface and may be a substrate for supporting, adhering, preserving, culturing and/or proliferating cells. The substrate for supporting cells includes, for example, a cell culture substrate (for example, a cell-culture container), a cell-preservation substrate or an implant substrate. The cells supported on the substrate for supporting cells herein is not particularly limited as long as they are adherent cells and include e.g., mammalian cells such as smooth muscle cells, endothelial cells, fibroblasts, osteoblasts and stem cells, and is preferably stem cells. The stem cells herein includes iPS cells, ES cells and mesenchymal stem cells as well as cells of mouse, rat, rabbit, dog, monkey and human, and preferably are mouse iPS cells and human iPS cells. The shape of the substrate for supporting cells herein can be appropriately selected depending upon the purpose, and includes, for example, a shape of plate, sheet, spherical, dish, chip or a desired tissue (for example, artificial bone or a surface part thereof). The substrate for supporting cells is preferably formed into a container for culturing or preserving adherent cells, more preferably, a container for culturing or preserving iPS cells.

The substrate for supporting cells herein contains a non-fluorine resin as a main component, and if necessary, may contain "another component". More specifically, the substrate may appropriately contain, if necessary, a substance contributing to cell adhesion, such as Matrigel (registered trade mark), laminin, collagen or fibronectin. The substrate for supporting cells herein preferably contains those another component at a half concentration of that required for culturing adherent cells (for example, iPS cells) on a non-fluorine resin based substrate for supporting cells which has not applied physical treatment such as an ozone/UV treatment (having no molecules except a main component of a non-fluorine resin on the cell supporting surface). For example, the substrate for supporting cells herein may contain Matrigel (registered trade mark) at a half or less concentration of, preferable at a 0.2 or less fold concentration of, that required for culturing iPS cells (for example, mouse iPS cells or human iPS cells) on a non-fluorine resin based substrate for supporting cells which has not applied physical treatment such as an ozone/UV treatment. Also, the substrate for supporting cells herein may contain laminin at a half or less concentration of that required for culturing iPS cells (for example, mouse iPS cells or human iPS cells) on a non-fluorine resin based substrate for supporting cells, which has not applied physical treatment such as an ozone/UV treatment.

The "non-fluorine resin" herein refers to a fluorine-free resin. Examples thereof may include a polyethylene, a super high molecular polyethylene, a polypropylene, a polystyrene, a polyvinyl chloride, polyvinyl alcohol, an acrylic resin, a polyethylene terephthalate, a polyacetal, a polycarbonate, a polyamide, a polyimide resin, a phenolic resin, an amino resin, an epoxy resin, a polyester and an acrylonitrile-butadiene-styrene copolymerized synthetic resin (ABS resin). Of them, a polystyrene is preferable. A polystyrene has stereoregularity (tacticity), and can be isotactic, syndiotactic and atactic forms. The form of polystyrene in the invention is not limited and can be any one of these forms or can be a mixture of two or more of these forms, and usually atactic form. Polystyrene is a high-molecular compound, and provided as various degrees of polymerization (average molecular weight). The polymerization degree is not limited in the invention and may be, e.g., 10 to 100,000 or 50 to 10,000. This means that polystyrene culture dishes supplied by various manufactures may be presumably different in material and physical properties. The invention has no limitation in material and physical properties, and can be use a culture dish provided by any manufacturer such as a tissue-culture dish of IWAKI (registered trade mark) (AGC TECHNO GLASS CO., LTD.).

The substrate for supporting cells of the invention has at least a part of cell supporting surface. The "cell supporting surface" herein means a surface capable of supporting, adhering, preserving, culturing and/or proliferating cells. The cell supporting surface does not always necessary for culturing or proliferating cells on it.

The cell supporting surface herein contains a component capable of generating a $C_7H_5O^+$ molecule (for example, a $(C_6H_5)C^+ (=O)$ molecule) by beam irradiation of a time-of-flight secondary ion mass spectrometer. The component capable of generating a certain molecule by beam irradiation of a time-of-flight secondary ion mass spectrometer may be a component which can be detected as a molecular-weight spectrum of the molecule by beam irradiation of a time-of-flight secondary ion mass spectrometer. The surface containing the component may be a surface obtained by applying UV to a polystyrene surface under ozone and humid atmosphere. The ratio of $C_7H_5O^+$ molecules relative to all molecules (regarded as 1) which are generated from the cell supporting surface by beam irradiation of a time-of-flight secondary ion mass spectrometer is preferably 0.01 or more (i.e., 1% or more), 0.015 or more (i.e., 1.5% or more), 0.016 or more (i.e., 1.6% or more), 0.017 or more (i.e., 1.7% or more), 0.018 or more (i.e., 1.8% or more), 0.019 or more (i.e., 1.9% or more) or 0.02 or more (i.e., 2% or more). Further, the cell supporting surface may preferably contain a component capable of generating $C_2H_3O^+$ molecules (for example, $^+CHO=CH_2$ molecule) by beam irradiation of a time-of-flight secondary ion mass spectrometer in a ratio of 0.45 or less (i.e., 45% or less), 0.5 or less (i.e., 50% or less), 0.55 or less (i.e., 55% or less) or 0.6 or less (i.e., 60% or less), as compared with all molecules generated by the beam irradiation of the cell supporting surface which are regarded as 1. Preferably, the cell supporting surface may have, the proportion of the ratio of the $C_2H_3O^+$ molecules to all molecules generated by beam irradiation of a time-of-flight secondary ion mass spectrometer to the ratio of the $C_7H_5O^+$ molecules to all molecules generated by beam irradiation using a time-of-flight secondary ion mass spectrometer, i.e., the value of (the ratio of the $C_2H_3O^+$ molecules to all molecules)/(the ratio of the $C_7H_5O^+$ molecules to all molecules), may be 0.45 or less (i.e., 45% or less), 0.46 or less (i.e., 46% or less), 0.47 or less (i.e., 47% or less), 0.48 or less (i.e., 48% or less), 0.485 or less (i.e., 48.5% or less), 0.49 or less (i.e., 49% or less), 0.5 or less (i.e., 50% or less), 0.55 or less (i.e., 55% or less) or 0.6 or less (i.e., 60% or less). The beam irradiation of a time-of-flight secondary ion mass spectrometer in this specification may be beam irradiation performed by using a time-of-flight secondary ion mass spectrometer (for example, PHI nanoTOF II, Ulvac-Phi Inc.), under condition of a primary ion beam for analysis of 30 kV Bi3++6.0 to 7.0 nA DC with the path width of 12 n-seconds and the frame-number of 64 to 75 times ($1\times10^{11}$ ions/cm$^2$), wherein neutralizing charge is set to be 10 eV electron beam +10 eV Ar$^+$.

In an embodiment, the cell supporting surface of the substrate for supporting cells of the invention has a C—C bond and/or a C—H bond caused a chemical shift. The "C—C bond and/or C—H bond caused a chemical shift" herein refers to a structure which binding state is changed by integration of an oxygen atom(s) into the molecular structure of a polystyrene, but does not contain oxygen atom. In other words, the C—C bond and/or C—H bond caused a chemical shift means a C—C bond and/or C—H which are not contained in a polystyrene, and means a structure except C—H, C—C and C-Ph. The contact angle of the cell supporting surface of the invention is low, although groups having an oxygen atom (e.g., OH, COOH, C=O) are very few. Thus, the low contact angle can be conceivably brought by a C—C bond and/or a C—H bond caused a chemical shift.

The carboxy group on a cell culture surface is considered to have an adverse effect on cells. The cell supporting surface of the substrate for supporting cells of the invention has an extremely low amount of carboxy group compared to a substrate for supporting cells treated with UV/ozone under the same conditions but non-humidification. Thus, the cell supporting surface of the substrate for supporting cells of the invention has substantially no carboxy groups. The "substantially no carboxy groups" herein does not mean no carboxy groups are present, but means that a carboxy group is not present to the extent that influences cell culture, and preferably, means that a carboxy groups are contained extremely low compared to the substrate for supporting cells treated with UV/ozone under the same condition but non-humidification, and more preferably, may mean that a carboxy group is virtually not detected or not detected in the a C (1s) narrow scan XPS spectrum.

In the substrate for supporting cells of the invention, the water contact angle with the cell supporting surface is a medium level, for example, 40 to 90°, 40 to 80°, 40 to 70°, 50 to 90°, 50 to 80°, 50 to 70°, 55 to 65° C., 60 to 90°, 60 to 80°, 60 to 70°, 70 to 90° or 70 to 80°; and preferably 70 to 90°. The contact angle herein is preferably determined by putting a drop of pure water (1 µL) on a sample and measuring in accordance with a θ/2 method by an automatic contact angle meter. The substrate for supporting cells of the invention has excellent preservation stability of the cell adhesion surface. Thus, the substrate for supporting cells of the invention is preferably keeps the aforementioned water contact angle range when stored airtight for 24 hours and a week after UV irradiation, and more preferably keeps the aforementioned water contact angle range when stored airtight for 24 hours and one month after UV irradiation. Thus, the substrate for supporting cells of the invention preferably maintains excellent cell adhesiveness after airtight storage for a week or a month from UV irradiation.

In an embodiment, the cell supporting surface of the substrate for supporting cells of the invention can support stem cells or enable the stem cells to proliferate in an undifferentiated state in the absence of feeder cells (scaffold cells) and coating with an extracellular matrix protein or in the presence of coating with a lower concentration of the extracellular matrix protein. For example, the cell supporting surface of the substrate for supporting cells of the invention may be a surface, on which 129/Ola system-derived mouse embryonic stem cells, i.e., EB3 cells (Mol. Cell biol. (2002) 22: 1526-36; Genes to Cell (2004) 9: 471-7) can successfully proliferate in the absence of feeder cells and coating with an extracellular matrix protein. Alternatively, the cell supporting surface may be a surface on which stem cells (for example, human iPS cells or mouse iPS cells) can successfully adhering or proliferating at a 0.2 fold concentration of Matrigel (registered trade mark) as compared to that required for a surface-untreated non-fluorine resin substrate. Alternatively, the cell supporting surface may be a surface on which stem cells (for example, human iPS cells or mouse iPS cells) can successfully adhering or proliferating at a 0.5 fold concentration of laminin as compared to that required for a surface-untreated non-fluorine resin substrate.

In an embodiment, the invention relates to a cell-culture container for adherent cells, comprising the above described substrate for supporting cells. The cell-culture container may have shapes of plate, sheet, spherical, dish, chip, fibrous or flask.

Advantageous Effects of Invention

In the method for producing a substrate for supporting cells of the invention, hydrophilicity can be stably imparted in a simpler manner. In addition, on the substrate for supporting cells of the invention, adherent cells including stem cells can be cultured without or with lower amount than before of a bio-derived material, that leads high stability, rare variance in results due to lot difference, and lower culturing cost. Further, since an animal-derived component is not used or is used in reduced amount, potential contamination can be reduced.

BRIEF DESCRIPTION OF DRAWINGS

FIG. 12B shows a graph showing the results of analysis of the surfaces of polystyrene dishes treated with ozone/UV for 3 minutes (3 min) and 5 minutes (5 min) by a time-of-flight secondary ion mass spectrometer (Ulvac-Phi Inc., PHI nanoTOF II). The vertical axis represents the count number and the horizontal axis represents mass-to-charge ratio (m/z).

FIG. 12C shows a graph showing the results of analysis of the surfaces of polystyrene dishes treated with ozone/UV for 10 minutes (10 min), and 20 minutes (20 min) by a time-of-flight secondary ion mass spectrometer (Ulvac-Phi Inc., PHI nanoTOF II). The vertical axis represents the count number and the horizontal axis represents mass-to-charge ratio (m/z).

DESCRIPTION OF EMBODIMENTS

Figure 1:
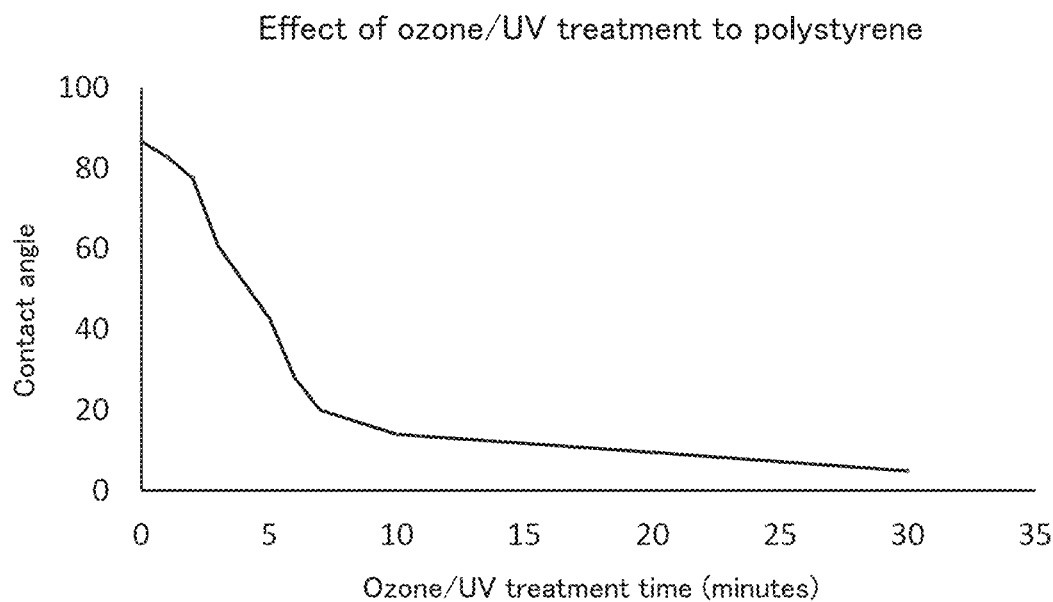
FIG. 1 is a graph showing a change of contact angle with time for ozone/UV treatment to a polystyrene. The vertical axis represents contact angle (°) and the horizontal axis represents ozone/UV treatment time (minutes).

1. Method for Producing a Substrate for Supporting Cells

The substrate for supporting cells of the invention can be produced by humidifying the periphery of a non-fluorine resin based substrate, and applying UV to the substrate under an oxygen and/or ozone atmosphere during and/or after humidification. Accordingly, in another embodiment, the invention relates to a method for producing a substrate for supporting cells comprising a humidification step of humidifying the periphery of a non-fluorine resin based substrate containing and applying UV to the substrate under an oxygen and/or ozone atmosphere during and/or after the humidification step.

(Humidification Step)

Humidification may be conducted in any manner as long as water vapor can be provided to the periphery of a non-fluorine resin based substrate. Humidification is achieved so that the surface of the substrate to be irradiated with UV is exposed to water vapor. Accordingly, the following UV irradiation step is performed under a humid environment. in the humidification step, it is not necessary to expose all surfaces of the substrate to water vapor. For example, humidification can be conducted by heating water in a container or an apparatus of a predetermined volume which is blocked from the outside air and contains said resin. The humidity after humidification (for example, humidity during UV irradiation) can be, for example, 20 to 60% RH, and preferably, 40 to 50% RH at 30° C. and 20 to 30% at 40° C. Humidification may be enough to provide an environment in which water vapor exist around the peripheral of the substrate during UV irradiation, or in which a substrate surface that is irradiated with UV is exposed to water vapor. Humidification can be conducted before and/or during UV irradiation, and preferably before and during UV irradiation.

(UV Irradiation Step)

UV irradiation is performed by irradiating said substrate with UV under oxygen and/or ozone atmosphere. UV to be applied may have an average wavelength of 184.9 nm and 253.7 nm. The wavelength of UV can be measured by a spectro-radiometer. UV can be irradiated in a UV illuminance of, for example, 2000 to 5000 W/cm², 2500 to 4500 µW/cm², 3000 to 4000 µW/cm², 3200 to 3800 µW/cm² or 3500 µW/cm². The distance from UV lamps to a plate is 2 to 6 cm, 3 to 5 cm, 3.5 to 4.5 cm, 3.6 to 4.4 cm, 3.7 to 4.3 cm, 3.8 to 4.2 cm, 3.9 to 4.1 cm or 4 cm. The UV irradiation can be performed for a time period until the water contact angle with a non-fluorine resin surface becomes, for example, 40 to 90°, 40 to 80°, 40 to 70°, 50 to 90°, 50 to 80°, 50 to 70°, 55 to 65° C., 60 to 90°, 60 to 80°, 60 to 70°, 70 to 90° or 70 To 80°. Alternatively, the UV irradiation time can be set to be 0.2 to 8 minutes, 0.2 to 5 minutes, 0.2 to 3 minutes, 0.5 to 8 minutes, 0.5 to 5 minutes, 0.5 to 3 minutes, 0.8 to 8 minutes, 0.8 to 5 minutes, 0.8 to 3 minutes, 1 to 8 minutes, 1 to 5 minutes or 1 to 3 minutes.

The oxygen atmosphere means that the oxygen concentration around the substrate is 80% or more (preferably, 90% or more). The oxygen atmosphere can be obtained by supplying oxygen (for example, 99% oxygen)(for example, dry oxygen) for a predetermined time (for example, 5 minutes) in the environment containing a substrate. Alternatively, the ozone atmosphere refers to an atmosphere having an ozone concentration of 400 ppm or more (preferably, 450 ppm or more). The ozone atmosphere can be obtained by supplying oxygen to a discharge ozone generator and supplying the generated ozone to an environment containing a substrate. Although ozone is also generated by UV irradiation in an oxygen atmosphere, chemical shift caused C—C bond and/or a C—H bond on the substrate surface increases more by UV irradiation in an ozone atmosphere, and thus UV is preferably applied in an ozone supplied atmosphere (including oxygen and ozone atmosphere).

The UV irradiation step cause chemical shift to a C—C bond and/or a C—H bond on the surface of substrate as well as lowers the water contact angle with the substrate surface to impart hydrophilicity. A carboxy group contributes to imparting hydrophilicity to a substrate surface, but is not suitable for culturing cells due to its highly reactivity. In the invention, since a carboxy group is rarely introduced into a substrate surface in the UV irradiation step, a hydrophilic surface become suitable for cell culturing.

Supporting cells on the substrate for supporting cells of the invention can be attained by adding the cells on the surface of the substrate for supporting cells in a medium suitable for the cells to be used, and culturing the cells to adhere for an appropriate time under conditions suitable for the cells. The cell proliferation using the substrate for supporting cells of the invention can be performed by culturing the cells which are supported on the substrate according to the above method for an appropriate time under conditions suitable for the cells.

2. Cell Culture Method Using a Substrate for Supporting Cells

In one aspect, the invention relates to a method for culturing adherent cells, comprising culturing the cells on the above described cell supporting surface of a cell-culture container. Usually, the cells can be cultured by adding a medium in a cell-culture container, seeding desired cells in the medium, and culturing the mixture of medium/cells in an incubator (usually, 5% $CO_2$, 37° C.) Culturing can be continued until the cells adhere or until the cells are divided to reach a desired number of cells, for example, for several hours to several weeks. In culturing for a long period, if necessary, the medium can be desirably exchanged.

In the method for culturing cells herein, the "medium" to be used can be appropriately selected from mediums known in the art depending upon the type of cell to be used. In culturing stem cells (for example, iPS cells), examples of the medium to be used include DMEM for mesenchymal cells, MSCBM for mesenchymal cells, a medium for EC cells, a medium for mesenchymal cells, a medium for ES cell, a medium for iPS cells, a medium for stem cells, iSTEM, Cellartis (registered trade mark) DEF-CS 500 XENO-Free Culture Medium, GS2-M (registered trade mark), GS1-R (registered trade mark) (those mentioned above are manufactured by Takara Bio Inc.); Poweredby10, Plusoid-M, G031101, M061101, SODATT201 (those mentioned above are manufactured by Glyco Technica Ltd.), ReproFF2, ReproNaive, RCHEMD001, RCHEMD001A, RCHEMD001B, ReproStem, ReproXF, ReproFF2, ReproFF, NutriStem (those mentioned above are manufactured by REPROCELL) and Stem fit medium (AJINOMOTO) such as StemFit (registered trade mark) AK02N.

In the method for culturing cells herein, the adherent cells to be cultured are not particularly limited, and are preferably stem cells (including iPS cells). Using the method for culturing of the invention, stem cells can be cultured in the absence of feeder cells and coating with an extracellular matrix protein (e.g., laminin, Matrigel (registered trade mark)), or in the presence of coating with a lower concentration of the extracellular matrix protein than conventional method, which contribute to avoid problems of low stability, variance in results due to lot difference or contamination in using a bio-derived material. In addition, when stem cells are cultured by the method for culturing cells of the invention, the intrinsic nature of stem cells (differentiation potential, and self-multiplication ability) can be maintained. Thus, the method for culturing cells of the invention can culture stem cells without using a bio-derived material, and can more stably prepare safe regenerative medical materials.

For example, the method for culturing of the invention may be a method comprising culturing cells on the above descried cell supporting surface of a cell-culture container, wherein the cells are cultured in the absence of feeder cells. Furthermore, the method for culturing of the invention may be a method comprising culturing cells in the presence of Matrigel (registered trade mark) at a concentration of 0.2 fold or more and less than one fold (for example, 0.2 fold to 0.9 fold, 0.2 fold to 0.8 fold, 0.2 fold to 0.7 fold, 0.2 fold to 0.6 fold, 0.2 fold to 0.5 fold, 0.2 fold to 0.4 fold, 0.2 fold to 0.3 fold, 0.2 fold, 0.3 fold to 0.9 fold, 0.3 fold to 0.8 fold, 0.3 fold to 0.7 fold, 0.3 fold to 0.6 fold, 0.3 fold to 0.5 fold, 0.3 fold to 0.4 fold, 0.3 fold, 0.4 fold to 0.9 fold, 0.4 fold to 0.8 fold, 0.4 fold to 0.7 fold, 0.4 fold to 0.6 fold, 0.4 fold to 0.5 fold, 0.4 fold, 0.5 fold to 0.9 fold, 0.5 fold to 0.8 fold, 0.5 fold to 0.7 fold, 0.5 fold to 0.6 fold or 0.5 fold) of that usually required for adhering stem cells on a surface-untreated non-fluorine resin based substrate. The "surface-untreated non-fluorine resin based substrate" herein refers to a substrate having a surface consisting only of a main component, i.e., a non-fluorine resin. Matrigel (registered trade mark) at a concentration (one fold) which is usually required for stem cell adhesion on a surface-untreated non-fluorine resin based substrate means a coating obtained by dissolving 170 µl of Growth factor reduced Matrigel (registered trade mark) (Corning) in 10 ml of DMEM-F12 medium (Life Technologies) and applying the mixture to a culture-dish surface at normal temperature for one hour.

The method for culturing of the invention may be characterized by culturing cells in the presence of laminin at a concentration of 0.2 fold or more and less than one fold (for example, 0.2 fold to 0.9 fold, 0.2 fold to 0.8 fold, 0.2 fold to 0.7 fold, 0.2 fold to 0.6 fold, 0.2 fold to 0.5 fold, 0.2 fold to 0.4 fold, 0.2 fold to 0.3 fold, 0.2 fold, 0.3 fold to 0.9 fold, 0.3 fold to 0.8 fold, 0.3 fold to 0.7 fold, 0.3 fold to 0.6 fold, 0.3 fold to 0.5 fold, 0.3 fold to 0.4 fold, 0.3 fold, 0.4 fold to 0.9 fold, 0.4 fold to 0.8 fold, 0.4 fold to 0.7 fold, 0.4 fold to 0.6 fold, 0.4 fold to 0.5 fold, 0.4 fold, 0.5 fold to 0.9 fold, 0.5 fold to 0.8 fold, 0.5 fold to 0.7 fold, 0.5 fold to 0.6 fold or 0.5 fold) of that usually required for adhering stem cells on a surface-untreated non-fluorine resin based substrate. The laminin at a concentration (1 fold) of usually required for stem cell adhesion on a surface-untreated non-fluorine resin based substrate means a coating obtained by diluting iMatrix (1 µg/µl) with PBS to obtain a final concentration of 0.5 µg/cm$^2$ and coating with the diluted solution at 37° C., 5% $CO_2$ in an incubator for one hour. Laminin herein is typically laminin 511E8.

The invention relates to a method for preserving adherent cells, comprising supporting cells on the above described cell supporting surface of a cell-culture container. Cells can be preserved by culturing cells on the cell supporting surface in accordance with the aforementioned method to adhere the cells to the surface and placing the cell-cultured container under appropriate preservation conditions. Preservation may be a temporary preservation for e.g., transfer, or long-term preservation for future use, and preferably is temporary preservation. The preservation conditions can be appropriately selected depending upon the purpose and the period of preservation.

EXAMPLES

The invention is more specifically described below by way of Examples. However, the invention is not limited to the Examples. All literatures cited throughout this application are incorporated in their entirety in this application by reference.

(Example 1) Change in Contact Angle by Ozone/UV Treatment to Resin Materials

Plates of a polytetrafluoroethylene (PTFE) (50×50 mm, thickness 1 mm, NICHIAS Corporation), a polyethylene (50×50 mm, thickness 1 mm, white), an acrylic resin (30×30 mm, thickness 3 mm, clear), an ABS resin (50×50 mm, thickness 0.5 mm, white), a polyethylene terephthalate (50×50 mm, thickness 0.3 mm, clear), a polypropylene (50×50 mm, thickness 0.5 mm, clear), a polycarbonate (50×50 mm, thickness 0.5 mm, clear) and a polystyrene (50×50 mm, thickness 0.45 mm, clear, Koeido) were set in an ozone/UV surface treatment apparatus, EKBIO-1100 (EBARA JITSUGYO CO. LTD., ozone generation lamps (6W×2), inner dimension of the tank: W240×H170×D175 (mm)/effective size W150×H80×D150 (mm)), and irradiated with UV of 184.9 and 253.7 nm at 40° C. under oxygen purge and humidification conditions for 10 minutes. The distance from UV lamps to each of the plates was 4 cm (UV illuminance was about 3500 µW/cm$^2$). After the treatment, contact angle was measured by putting a drop of pure water (1 µL) on a sample and using an automatic contact angle meter DMs-200 (Kyowa Interface Science Co., Ltd.) in accordance with the θ/2 method.

The results are shown in Table 1. It was confirmed that the contact angles of all materials except PTFE increase by the ozone/UV treatment under a humid environment.

TABLE 1

| Material | Non treatment | UV treatment (10 minutes) |
| --- | --- | --- |
| PTFE | 109.2 | 107.5 |
| Polyethylene | 90.9 | 68.5 |
| Acrylic resin | 65.8 | 56.2 |
| ABS resin | 97.5 | 70.1 |
| Polyethylene terephthalate | 80.2 | 34.0 |
| Polypropylene | 96.0 | 81.3 |
| Polycarbonate | 89.0 | 45.9 |
| Polystyrene | 87.6 | 21.6 |

(Unit: °)

(Example 2) Change in Contact Angle with Ozone/UV Treatment Time to Polystyrene

A polystyrene plate (50×50 mm, thickness 0.45 mm, model: TP-45, clear (Koeido)) was set in an ozone/UV surface treatment apparatus, EKBIO-1100 (EBARA JITSUGYO CO., LTD.) and irradiated with UV of 184.9 and 253.7 nm at 30° C. in the air under humidification conditions for one minute to 30 minutes. The distance from UV lamps to each of the plates was 4 cm (UV illuminance was about 3500 µW/cm$^2$). After the treatment, contact angle was measured by putting a drop of pure water (1 µL) on a sample and using an automatic contact angle meter DMs-200 (Kyowa Interface Science Co., Ltd.) in accordance with the θ/2 method, in the same manner as in Example 1.

The results are shown in FIG. 1. It was confirmed that contact angle decreases with time of the ozone/UV treatment. The water contact angle fell within the range of 40 to 700 when the ozone/UV treatment time was one minute to 3 minutes.

(Example 3) Effect of Humidification and Ozone on Change in Contact Angle with Polystyrene Dish by UV Treatment Four polystyrene dishes (No. 430589, Corning Incorporated, Massachusetts, USA) were set in an ozone/UV surface treatment apparatus, EKBIO-1100 (EBARA JITSUGYO CO., LTD.), treated in following groups of condition, and investigated difference in contact angles.

(1) a group of dishes purged with ozone at 40° C. under discharge ozone generation for 5 minutes, and irradiated with UV beams of 184.9 and 253.7 nm under humidification conditions for 10 minutes;

(2) a group of dishes purged with ozone at 40° C. under discharge ozone generation for 5 minutes, and irradiated with UV beams of 184.9 and 253.7 nm under non-humidification conditions for 10 minutes;

(3) a group of dishes purged with oxygen at 40° C. for 5 minutes, and irradiated with UV beams of 184.9 and 253.7 nm under humidification conditions for 10 minutes (no discharge ozone generation);

(4) a group of dishes purged with oxygen at 40° C. for 5 minutes, and irradiated with UV beams of 184.9 and 253.7 nm under non-humidification conditions for 10 minutes (no discharge ozone generation); and (5) a group of dishes without ozone/UV treatment.

The distance from UV lamps to each of the plates was set to be 4 cm (UV illuminance: 3500 µW/cm$^2$). After the treatment, contact angle was measured by putting a drop of pure water (1 µL) on a sample and using an automatic contact angle meter DMs-200 (Kyowa Interface Science Co., Ltd.) in accordance with the θ/2 method, in the same manner as in Example 1.

Average values of individual treatment groups are shown in Table 2. The results show that, in treating polystyrene plates with UV for the same duration, the contact angle changed largest by treatment under ozone generation and a humid environment.

TABLE 2

|  | (1) | (2) | (3) | (4) | (5) |
| --- | --- | --- | --- | --- | --- |
| Oxygen supply | + | + | + | + | − |
| Oxygen supply by discharge oxygen generator | + | + | − | − | − |
| Humidification | + | − | + | − | − |
| UV irradiation | + | + | + | + | − |
| Contact angle (°) | 18.3 | 26.0 | 15.8 | 24.0 | 90.4 |

(Example 4) Effect of Humidification on Ozone Concentration in Tank

To investigate the effect of humidification on ozone concentration in a tank, the following experiment was conducted both of in the presence and absence of humidification. Using an ozone/UV surface treatment apparatus, EKBIO-1100 (EBARA JITSUGYO CO., LTD.), ozone was supplied (ozone purge) by a discharge ozone generator for 5 minutes. Subsequently, while maintaining ozone supply, irradiation was performed with UV of 184.9 nm and 253.7 nm for 10 minutes. Thereafter, ozone supply and UV irradiation were terminated. Ozone concentration was measured from the initiation of ozone purge to 10 minutes after termination of ozone supply and UV irradiation. The ozone concentration was measured by an ultraviolet absorption ozone concentration meter, type PG-620 (EBARA JITSUGYO CO., LTD.). In all steps, the inner temperature of the tank was set at 40° C.

Figure 2:
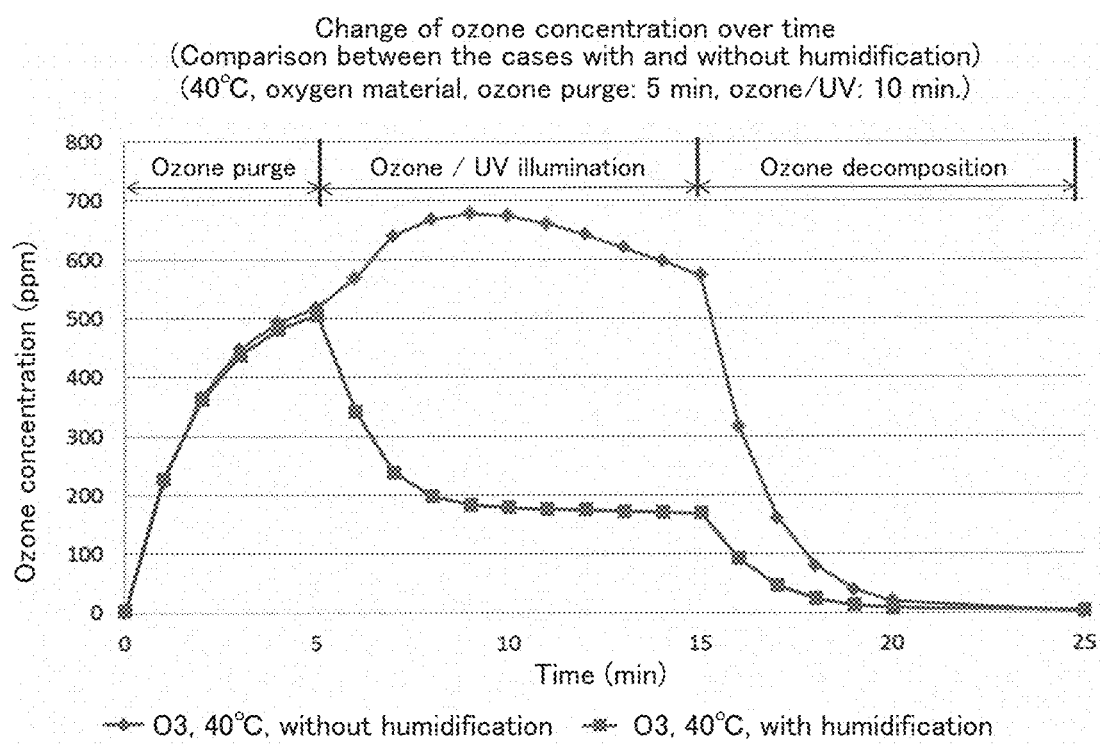
FIG. 2 is a graph showing a change of ozone concentration in the container with or without humidification. The vertical axis represents ozone concentration (ppm) and the horizontal axis represents passage of time (minutes). In the time represented by the horizontal axis, the time period of 0 to 5 minutes is a period for ozone purge treatment, the time period of 5 to 15 minutes is a period for UV irradiation, and the time period of 15 to 25 minutes is a period for ozone decomposition in the treatment container. Diamond marks represent without humidification; square marks represent with humidification.

The change of ozone concentration with time is shown in FIG. 2. It was shown that the ozone concentration increases by UV irradiation without humidification, whereas ozone concentration conversely decreases after UV irradiation in the humidification condition, though the UV wavelength includes the ozone generation wavelength (184.9 nm). Thus, it was suggested that UV irradiation energy is used in reactions except an ozone generation reaction under a humid environment, thereby resulted in the change in the contact angle and cell adhesiveness/proliferation. For example, it is known that water molecules constituting water vapor generate hydrogen atoms and hydroxy radicals by UV irradiation. Since hydroxy radicals are highly reactive, the generated hydroxy radicals interact with molecules on a polystyrene surface and conceivably changes the nature of the surface.

(Example 5) Measurement of Humidity in Tank Under Humidification Conditions

An ozone/UV surface treatment apparatus, EKBIO-1100 (EBARA JITSUGYO CO., LTD.) was used at an in-tank temperature of 40° C. or 30° C. under humidification conditions. The humidity of the apparatus was measured by a temperature/humidity sensor, WATCH LOGGER KT-300/KT-275 (Fujita Electric Works, Ltd.) every minute for 30 minutes.

In all temperatures, the relative humidity in the tank under humidification conditions was almost constant. The relative humidity fell within the range of 20 to 40% at an in-tank temperature of 40° C., whereas the relative humidity fell within the range of 30 to 50% at an in-tank temperature of 30° C.

(Example 6) Time-Dependent Change of Contact Angle with Polystyrene Dish Treated with Ozone/UV To confirm whether the contact angle obtained by the ozone/UV treatment is maintained after passage of a time, the contact angle was measured one day, one week and a month after the ozone/UV treatment. 60 mm-diameter untreated polystyrene dishes (No. 430589, manufactured by Corning Incorporated, Massachusetts, USA) was irradiated with UV using an ozone/UV surface treatment apparatus, EKBIO-1100 (EBARA JITSUGYO CO., LTD.) for one minute, 2 minutes, 3 minutes, 5 minutes, 10 minutes, 20 minutes or 30 minutes at a distance of 4 cm from a UV lamp under humidification conditions after oxygen purge for 5 minutes at 40° C. After the treatment, the plates were enclosed in a plastic bag and stored at room temperature for 24 hours, one week and a month. After the storage, the contact angle was measured in the same manner as in Example 1.

Individual dishes were tested for cell adhesion and proliferation. A mouse ES cells, 129/Ola system-derived mouse embryonic stem cells, EB3 cells (Mol. Cell biol. (2002) 22: 1526-36; Genes to Cell (2004) 9: 471-7), were obtained from Riken Cell Bank (Japan). In the cells, one of the Oct3/4 genes (one of gene loci), which is one of the undifferentiated cell specific genes, is replaced by an ires-blasticidin S resistant gene, and thus, a blasticidin S resistant gene is expressed under transcription activation of the Oct3/4 gene. Thus, when EB3 cells are differentiated and the Oct3/4 gene does not express, EB3 cells do not proliferate in the presence of blasticidin.

EB3 cells in a frozen ampule were thawed in a constant-temperature bath for 2.5 minutes and centrifuged to prepare a cell suspension of 10 ml. Two flasks (25 cm$^2$) each containing a 0.1% gelatin solution (5 ml) were incubated in an incubator for 30 minutes or more at 5% $CO_2$ at 37° C. Then, the gelatin solution was suctioned by a Pasteur pipette to coat the culture surface of the flasks with gelatin. To each of the flasks having a gelatin coating, the cell suspension (5 ml) of EB3 cells prepared above was seeded and designated as primary cells (P0). The primary cells obtained were cultured in an incubator for 3 days while exchanging the medium with 200 ml of a fresh ES cell culture liquid (composition: 100 ml of GMEM medium, 1 ml of MEM non-essential amino acids (NEAA), 1 ml of sodium pyruvate, 1 ml of 2-mercaptoethanol, 100 µl of a leukocyte proliferation inhibitory factor, 100 µl of a blasticidin S solution, in 100 ml, the same applies below) every day.

Three days after culture, the culture liquid was removed from each of the flasks and the flasks were washed with PBS (5 ml per flask). Thereafter, 0.25% trypsin (2.5 ml) was added to each flask and the flasks were incubated in an incubator for two minutes. The cells remaining on the culture surface were completely suspended in trypsin by pipetting. The resultant cell suspending trypsin solution from the two flasks and a culture liquid (5 ml) were added to a 50-ml tube to adjust the total amount to be 10 ml. The tube was centrifuged at 1500 rpm for 5 minutes and cells were collected as a precipitate. To the collected cells, a fresh culture liquid was added. The mixture was blended by pipetting to prepare a cell suspension. To each of 24 culture dishes, a culture medium (3 ml) was added, and the diluted cell suspension (2 ml) was seeded at final number of cells of $3.1 \times 10^5$ cells/dish, and cultured in an incubator for three days. Every day during a culture period, photomicrographs of culture dishes were taken and appearance of EB3 cells proliferated was observed. Thereafter, the culture liquid was removed from dishes, which were washed with PBS (5 ml). Trypsin (1 ml) was added, the dishes were incubated in an incubator for 5 minutes, and then the remaining cells on the culture surface were completely suspended in trypsin by pipetting. The cells suspending trypsin solutions obtained from the individual dishes were transferred to micro tubes (24 tubes in total) and cryopreserved at −80° C.

On the next day, the cells were thawed by ultrasonic wave treatment of the micro tubes to destroy the cell membrane. The DNA contents in samples were measured to calculate the number of cells. The total DNA content of each sample was determined from fluorescence intensity measured by fluorescence spectrophotometer (Qubit (registered trade mark) 2.0 Fluorometer, LIFE TECHNOLOGIES, Japan) according to the manufacturer's protocol and referring to a calibration curve, which was prepared by using a standard sample. The total DNA content was divided by DNA content per cell (7.7 pg) to obtain the number of cells in each of the culture dishes on Day 3 of culture. A significant difference test of the cell numbers was determined in accordance with the Turkey-Krammer Test at a significance level of 0.05.

Figure 3:
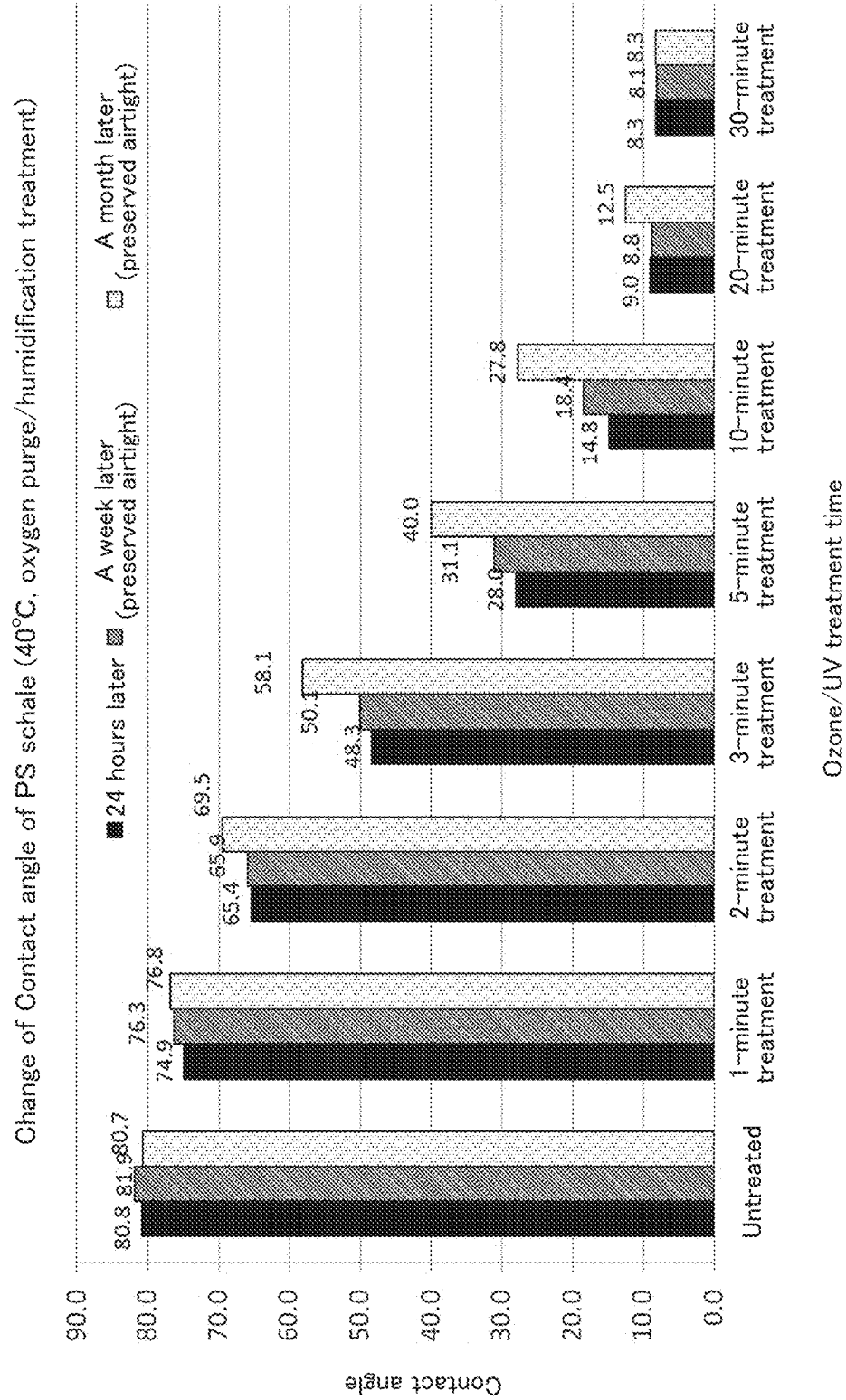
FIG. 3 is a graph showing a change of contact angle during long-term preservation. The vertical axis represents contact angle (°) and the horizontal axis represents ozone/UV treatment time. In each group, the bars represent contact angles after storage for 24 hours, one week, and one month, from left to right.

A change in contact angle is shown in FIG. 3. It was found that the contact angle tends to gradually increase with the passage of time from Day 1, one week to one month after ozone/UV treatment, but sharp increase was rarely observed. Investigation of adhesion of cells indicated that the adhesions to dishes after 1 day and one-week preservation are just the same as that of the day of hydrophilic treatment (day 0). It was confirmed that cells cultured on the dish preserved for one month showed slight morphological changes, but sufficient cell adhesion is maintained.

(Example 7) Culture of ES Cells on Treated Plates (1) Plate Preparation

As a negative control, a 60 mm-diameter polystyrene dish not treated with UV (No. 430589, Corning Incorporated, Massachusetts, USA) (TCPS) was used. As a positive control, a gelatin-coated polystyrene dish (AGC TECHNO GLASS CO., LTD., JAPAN; 3010-060) (Treated PS) was used. As UV treatment groups, 60 mm-diameter untreated polystyrene dishes (No. 430589, Corning Incorporated, Massachusetts, USA) were irradiated with UV beams of 184.9 nm and 253.7 nm by using an ozone/UV surface treatment apparatus, EKBIO-1100 (EBARA JITSUGYO CO., LTD.) under the following conditions: UV irradiation (UVPS (1 m)) at 25° C. under atmospheric air (no humidification and no ozone purge) for one minute; UV irradiation (UVPS (3 m)) at 25° C. under atmospheric air (no humidification and no ozone purge) for 3 minutes; UV irradiation ($O_2H$ (+) PS) under humidification for 3 minutes after oxygen purge at 40° C. for 5 minutes; UV irradiation ($O_2H$ (−) PS) in a dry state (no humidification) for 3 minutes after oxygen purge at 40° C. for 5 minutes; UV irradiation ($O_3H$ (+) PS) under humidification for 3 minutes, after ozone purge at 40° C. for 5 minutes; and UV irradiation ($O_3H$ (−) PS) in a dry state (no humidification) for 3 minutes after ozone purge at 40° C. for 5 minutes. During the ozone/UV treatment, the ozone concentration was measured in the same manner as in Example 4.

(2) Measurement of Contact Angle

The contact angles to the plates (except Treated PS) prepared in Example 7 (1) were measured in the same manner as in Example 1. The contact angle was obtained by measuring contact angles at 5 sites on the same plate and obtaining an average value of them.

(3) Culture of Mouse ES Cells

Mouse ES cells were cultured in the same manner as in Example 6 and the number of cells was calculated from the DNA content after culture.

(4) Results

Figure 4:
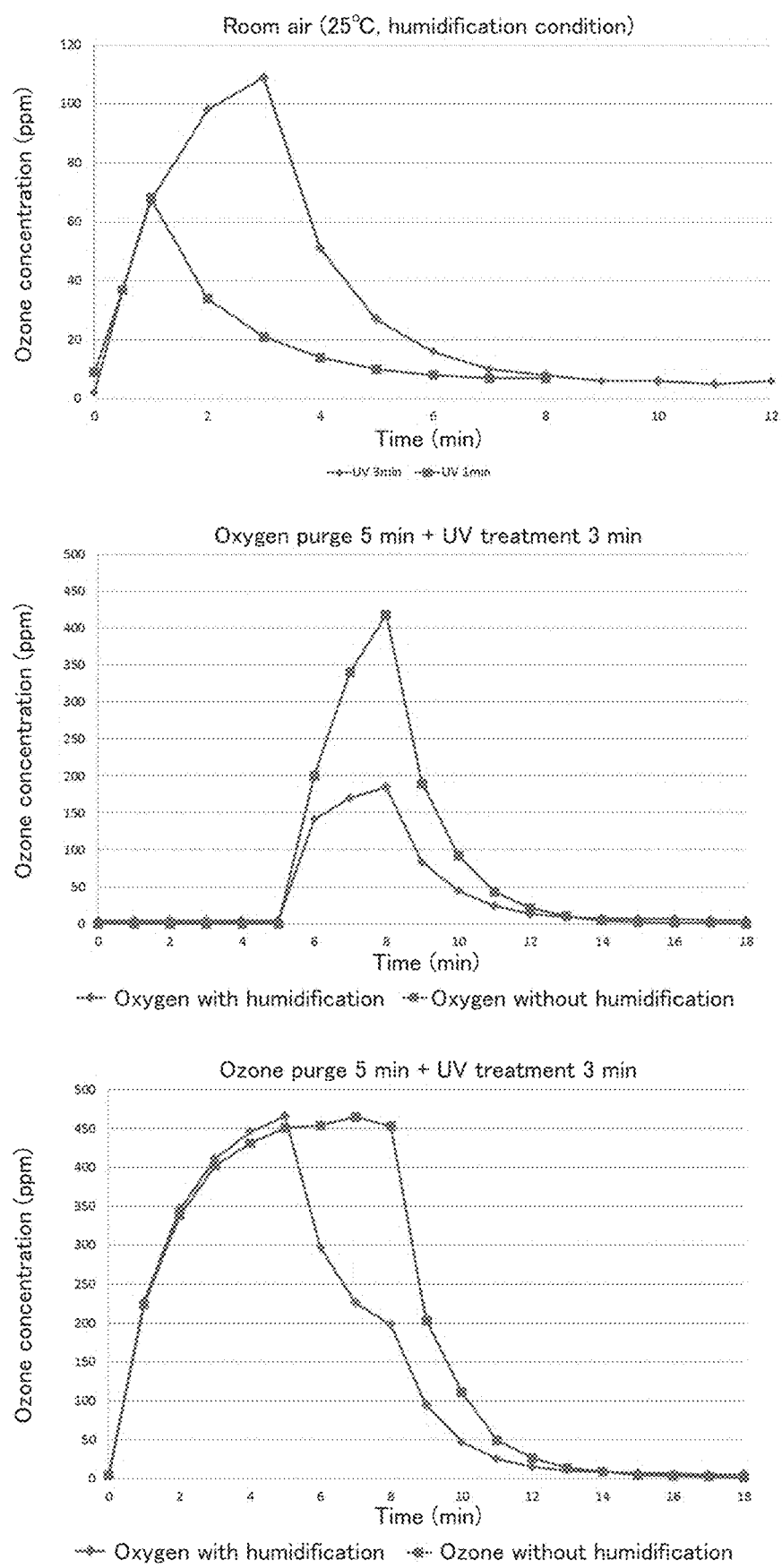
FIG. 4 shows graphs showing a change of ozone concentration during ozone/UV treatment to a polystyrene dish. The graphs show UV treatment for 1 or 3 minutes alone (indoor air, 25° C., humidification), UV treatment for 3 minutes after 5-minute oxygen purge, and UV treatment for 3 minutes after 5-minute ozone purge, from top to bottom. In each graph, the vertical axis represents ozone concentration (ppm) and the horizontal axis represents treatment time. In the top graph, the UV is treated from time 0 to 1 minute (UV 1 min) or from time 0 to 3 minutes (UV 3 min), whereas in the two graphs below it, UV is treated from time 5 to 8 minutes. In the middle graph, oxygen was purged during the time period of 0 to 5 minutes. In the bottom graph, ozone was purged during the time period of 0 to 5 minutes.
Figure 5:
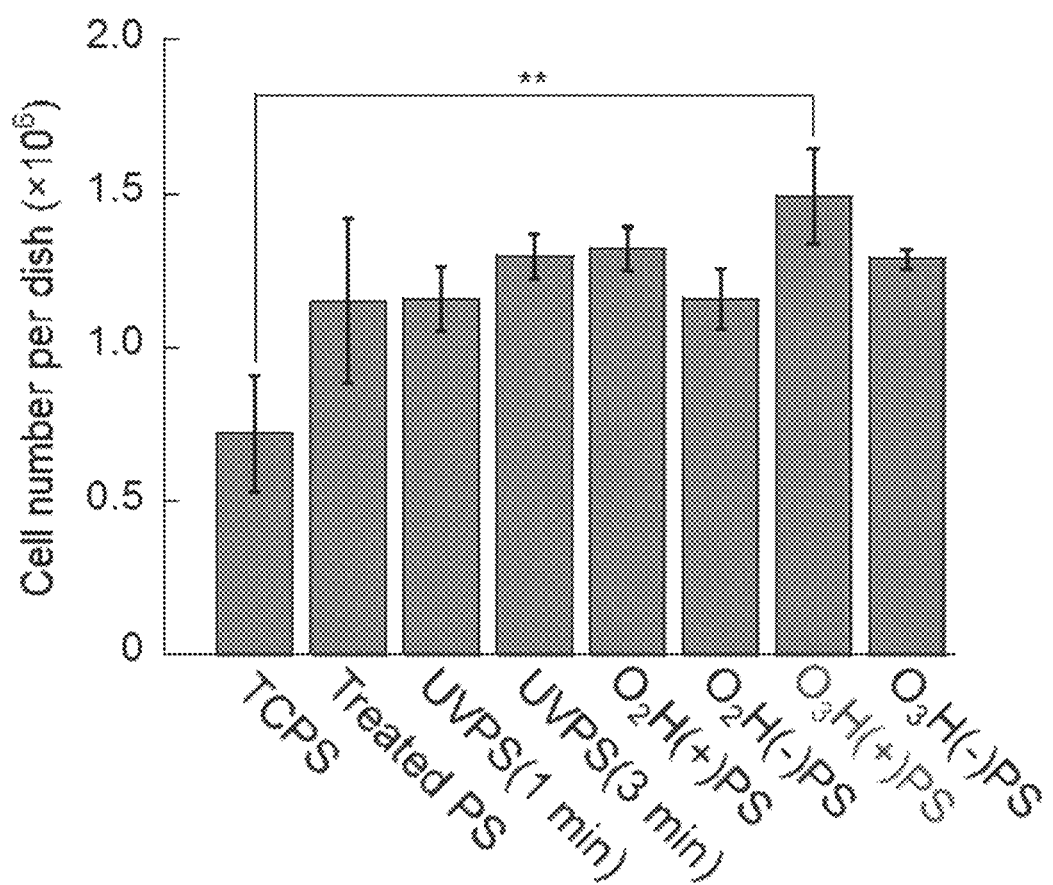
FIG. 5 is a graph showing the number of cells after culturing EB3 cells, mouse ES cells, on various dishes for 3 days. The vertical axis represents the number of cells ($\times 10^5$ cells/dish). The horizontal axis represents, from left to right, a UV untreated polystyrene dish (negative control)(TCPS); a gelatin-coated polystyrene dish (positive control) (Treated PS); a polystyrene dish irradiated with UV for one minute at 25° C. under an the atmospheric environment (no humidification and no ozone purge) (UVPS (1 min)); a polystyrene dish irradiated with UV for 3 minutes at 25° C. under the atmospheric environment (no humidification and no ozone purge) (UVPS (3 min)); a polystyrene dish irradiated with UV for 3 minutes at 40° C. under humidification (oxygen purge) ($O_2H$ (+) PS); a polystyrene dish irradiated with UV for 3 minutes at 40° C. in a dry state (no humidification, oxygen purge) ($O_2H$ (−) PS); a polystyrene dish irradiated with UV for 3 minutes at 40° C. under humidification (oxygen purge) ($O_3H$ (+) PS); and, a polystyrene dish irradiated with UV for 3 minutes at 40° C. in a dry state (no humidification, oxygen purge) ($O_3H$ (−) PS). ** represents $P<0.05$ and error bars represent standard errors.
Figure 6A:
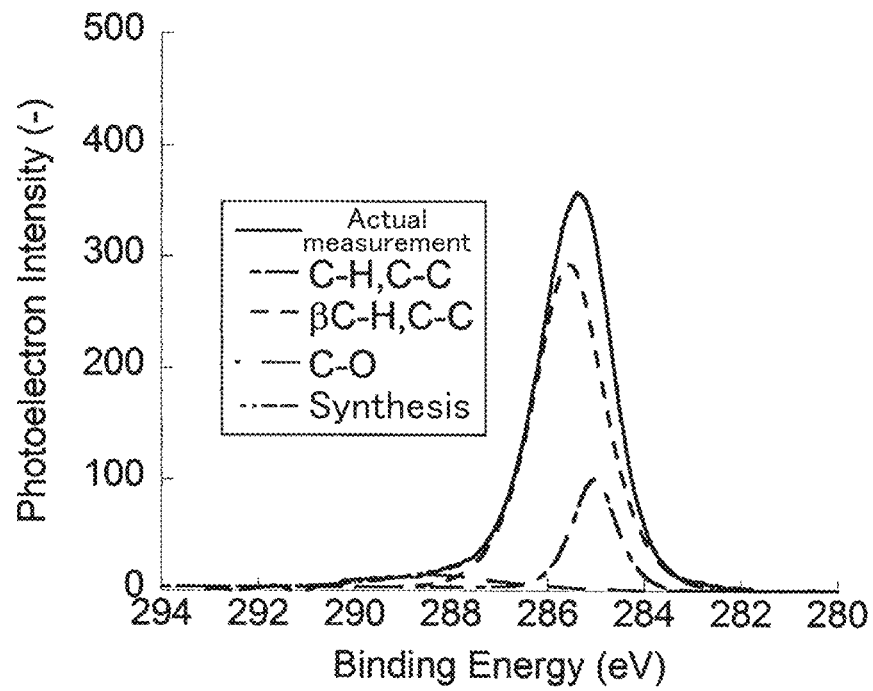
FIG. 6A is a graph showing the results of XPS analysis on the surface of a polystyrene dish treated in accordance with Example 3, (1).
Figure 6B:
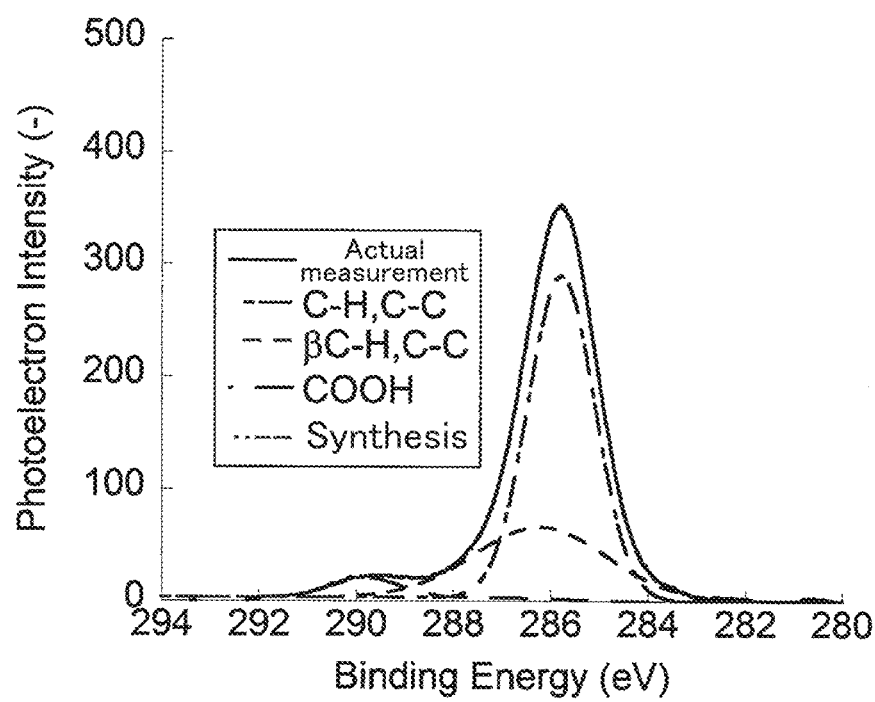
FIG. 6B is a graph showing the results of XPS analysis on the surface of a polystyrene dish treated in accordance with Example 3, (2).
Figure 6C:
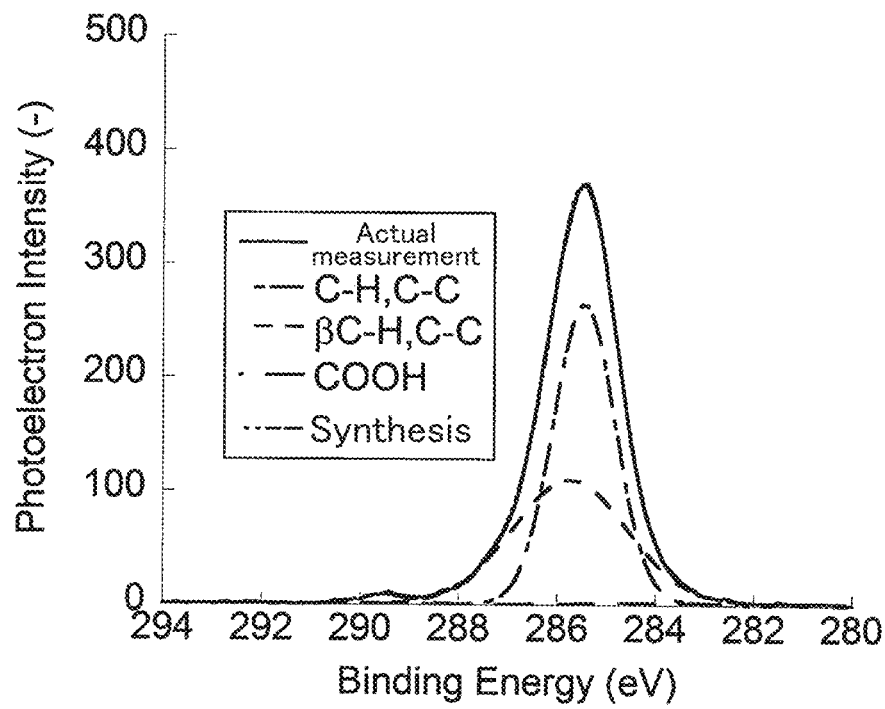
FIG. 6C is a graph showing the results of XPS analysis on the surface of a polystyrene dish treated in accordance with Example 3, (3).
Figure 6D:
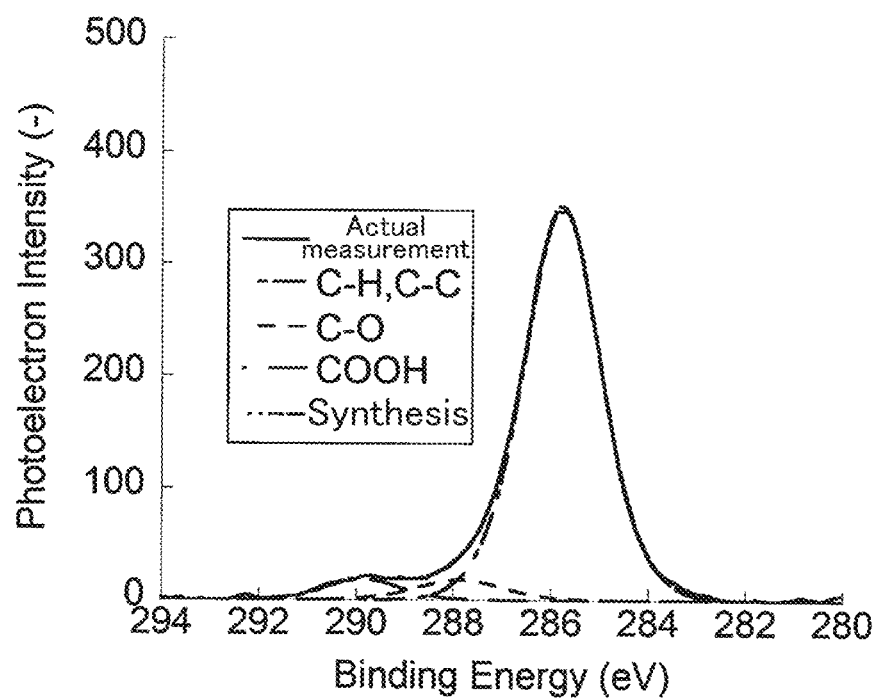
FIG. 6D is a graph showing the results of XPS analysis on the surface of a polystyrene dish treated in accordance with Example 3, (4).

Changes of ozone concentration during treatment of the plates are shown in FIG. 4. The conditions and the contact angles of individual plates are shown in Table 3. Calculation results of the number of cells at Day 3 of culturing are shown in FIG. 5. The cell proliferation was the largest on dishes treated under an ozone environment with humidification. Thus, it was demonstrated that a surface on which a larger number of adherent cells can adhere, can be obtained by applying UV to a polystyrene plate under an ozone environment with humidification.

TABLE 3

| Plate | TCPS | UVPS (1 m) | UVPS (3 m) | $O_2H$ (+) PS | $O_2H$ (−) PS | $O_3H$ (+) PS | $O_3H$ (−) PS |
|---|---|---|---|---|---|---|---|
| UV irradiation | − | + | + | + | + | + | + |
| Irradiation time (minutes) | — | 1 | 3 | 3 | 3 | 3 | 3 |
| Atmosphere | — | Atmospheric air | Atmospheric air | $O_2$ | $O_2$ | $O_3$ | $O_3$ |
| Humidification | − | − | − | + | − | + | − |
| Contact angle (°) | 82.2 | 77.2 | 47.9 | 49.2 | 58.5 | 39.6 | 48.3 |
| SD | 0.5 | 1.5 | 1.0 | 1.0 | 0.5 | 0.7 | 1.3 |

(Example 8) Analysis of Functional Groups on Plate Surfaces Treated

In order to investigate the relation between cell adhesion and surface functional groups, change of surface functional groups of polystyrene plates by the presence or absence of an ozone environment, the presence or absence of humidification conditions, and the presence or absence of UV irradiation was analyzed.

Polystyrene dishes (Corning Incorporated, Massachusetts, USA; 430589) were prepared in the same manner as in Example 3 (1) to (4) except that the UV irradiation time was set at 3 minutes. From each of the dishes, plates of 8 mm-squares were cut out and the surface of the plates was analyzed by using a photoelectron spectrometer (JEOL Ltd., JPS-9010). Each sample was attached to a sample table and the sample table was placed in the preparation chamber, which was vacuumed. Thereafter, the sample table was inserted in the measuring room. Since the sample to be used in this analysis was made of polystyrene, constituent elements are carbon and oxygen (hydrogen is one of constituent elements, but hydrogen has only one electron and thus cannot be measured by XPS). Thus, in this analysis, wide scan was not performed and a narrow scan spectrum of electrons of is-orbit of carbon was obtained. As X-ray, AlKa beam (1486.6 eV) was used. The measurement range of carbon narrow scan was set to be 294.0 to 280.0 eV. The step width was set to be 0.1 eV and cumulated count was set at 10. After obtaining the spectrum, smoothing of the spectrum was performed by repeating a smoothing step for five times. Electrons scattered by inelastic scattering, and background of a spectrum generated due to noise were removed by using the Shirley background removal. The waveform separation of a spectrum was performed by approximation of a component waveform with normal-distribution Gauss-Lorentzian function.

The results of surface analysis of the polystyrene dishes treated in accordance with Example 3 (1) to (4) are shown in FIG. 6A to FIG. 6D, respectively. From these results, it was found that a group having an oxygen atom, such as a hydroxyl group, a carbonyl group and a carboxy group, which conceivably contributes to hydrophilicity, was present in UV irradiation groups under non-humidification conditions, whereas groups having an oxygen atom unexpectedly did not virtually change in the UV irradiation groups under humidification conditions. Further, only in the UV irradiation groups under humidification conditions, a C—C bond and a C—H bond were observed to be caused a chemical shift (C—C, C—H (Modified)). Thus, it was demonstrated that the C—C bond and the C—H bond (C—C, C—H (Modified)), which are not introduced by a conventional ozone/UV treatment but are introduced by humidification in combination with supply of ozone, contribute to improvement of adhesion and proliferation of cells.

(Example 9) Culture of Mouse iPS Cells on Plate Treated with Ozone/UV

Figure 7:
FIG. 7 shows pictures of mouse iPS cells cultured for 3 days on various dishes. Of each pair of pictures, the upper picture shows an optical micrograph and the lower picture shows a fluorescence micrograph. The pictures in the upper stage show the results of cell culture on dishes without ozone/UV treatment; and the pictures in the lower stage show the results of cell culture on dishes with ozone/UV treatment. In the upper stage, the left pictures show the results of mouse iPS cells cultured on feeder cells, and the right pictures show the results in the absence of both feeder cells and gelatin. In the lower stage, the pictures show the results of mouse iPS cells cultured on dishes treated with ozone/UV for one minute, 3 minutes, and 10 minutes, from left to right (all were cultured in the absence of both feeder cells and gelatin).
Figure 7:
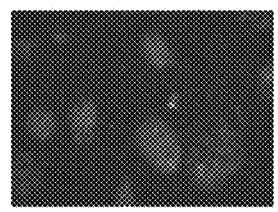
Figure 7:
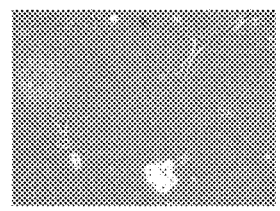
Figure 7:
Figure 7:
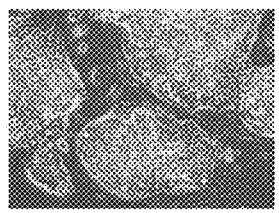
Figure 7:
Figure 7:
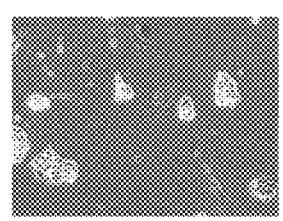

From the above study, it was demonstrated that UV irradiation under an ozone environment in humidification conditions is important to form a surface suitable for adhesion of adherent cells. To further investigate UV treatment time suitable for providing a surface suitable for culture of iPS cells, adhesion of mouse iPS cells onto polystyrene plates treated with UV in different time periods was tested.
(1) Preparation of Plate
Using an ozone/UV surface treatment apparatus, EKBIO-1100 (EBARA JITSUGYO CO., LTD.), 60 mm-diameter polystyrene cell-culture dishes (No. 430589, manufactured by Corning Incorporated, Massachusetts, USA) were irradiated with UV of 184.9 nm and 253.7 nm as follows: oxygen purge was performed at 40° C. for 5 minutes, and thereafter, UV was applied one minute, 3 minutes or 10 minutes under humidification, and a plate not irradiated with UV was used as a negative control.
(2) Culture of Mouse iPS Cells
Mouse iPS cells (RIKEN CELL BANK, APS0001 strain, passaged 6 times) having a GFP gene under control of a Nanog promoter were seeded on DMEM (15% FBS, 0.1 mm NEAA, 0.1 mM 2-mercaptoethanol, 1000 U/ml mouse LIF) in the polystyrene dishes prepared in the step (1) (feeder cell-free, gelatin-free). After the cells cultured for 3 days, the non-adherent cells were removed and the adherent cells were observed by a microscope. As a positive control, mouse iPS cells were cultured in the same conditions except that the surface of dish was not treated with ozone/UV, and that the cells are cultured on feeder cells (MEF cells).
(3) Results
Photomicrographs and fluorescence micrographs of mouse iPS cells adhered to a polystyrene dish having a surface treated with ozone/UV are shown in FIG. 7. Since almost all cells express GFP, it was demonstrated that cells maintain undifferentiation potential. It was shown that, although feeder cells and gelatin were not contained, the number of adherent cells on ozone/UV treated surface for one minute and 3 minutes are the same as the number of adherent cells cultured on feeder cells.

(Example 10) Culture of Human iPS Cells on Plate Treated with Ozone/UV (Study on Matrigel (Registered Trade Mark) Concentration)

Since mouse iPS cells were successfully cultured on a polystyrene dish having a ozone/UV treated surface in the absence of feeder cells and gelatin, whether the concentration of Matrigel (registered trade mark) can be reduced or not was investigated with respect to human iPS cells.

Figure 8:
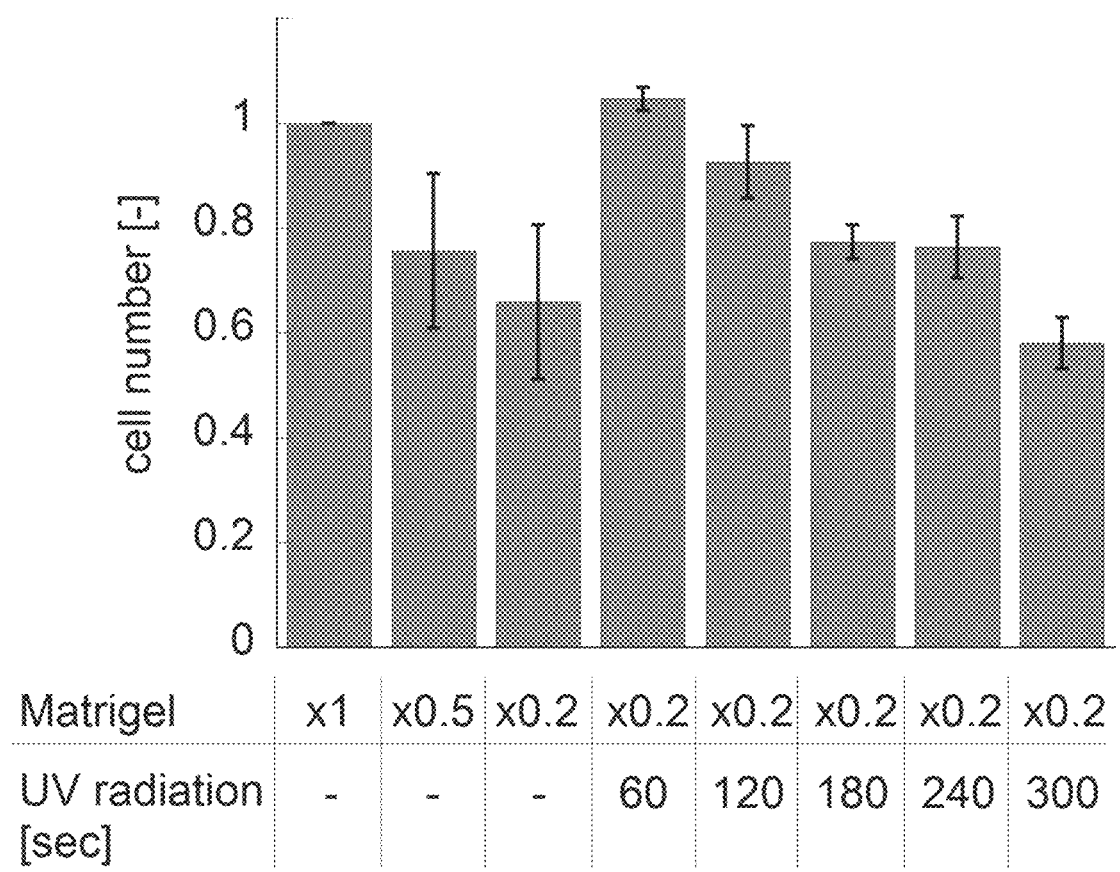
FIG. 8 is a graph showing the number of adhered cells after culturing human iPS cells (201B7) on polystyrene dishes with various concentration of Matrigel (registered trade mark) for 5 days. The vertical axis represents the ratio of the number of cultured cells relative to the number of cells cultured in the presence of 100% Matrigel (registered trade mark) which is regarded as 1. The upper-stage under the horizontal axis (Matrigel) indicates the concentration of Matrigel (registered trade mark), which is represented by ratio (fold) relative to the recommended concentration which is regarded as 1. The lower-stage under the horizontal axis indicates the time period (seconds) of ozone/UV treatment (UV irradiation) to a polystyrene dish (UV irradiation [sec]) (lower stage). In the lower-stage under the horizontal axis, a bar (−) represents no UV treatment. Error bars represent standard errors.
Figure 9:
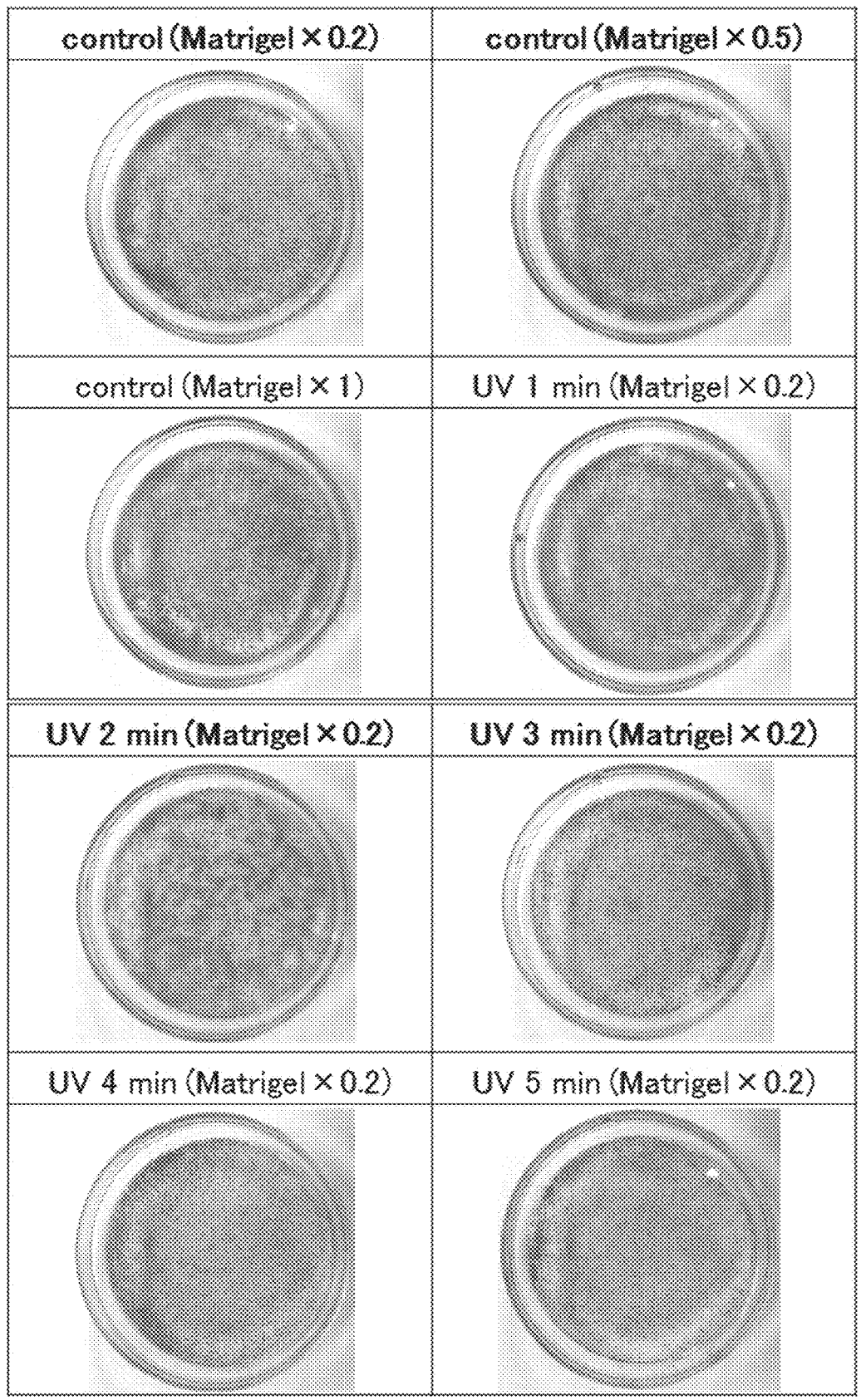
FIG. 9 shows pictures of adhered cells after culturing human iPS cells (201B7) on polystyrene dishes in the presence of various concentration of Matrigel (registered trade mark) for 5 days. The top pictures show the results of culturing on ozone/UV untreated dishes with Matrigel (registered trade mark) at concentrations of 0.2 fold (left) and 0.5 fold (right) of the ordinary culture. In the second row, the left picture shows the results of culturing on a ozone/UV untreated dish with Matrigel (registered trade mark) at a concentration of ordinary culture (1 fold). In the second row, the right picture shows the results of culturing on an ozone/UV treated dish (UV irradiation: one minute) with a Matrigel (registered trade mark) at a 0.2 fold concentration of the ordinary culture. The pictures in the third row and fourth row show the results of culturing on ozone/UV treated dishes with Matrigel (registered trade mark) at 0.2 fold concentration of the ordinary culture. In the third row, left shows 2-minute UV irradiation and the right shows 3-minute UV irradiation. In the fourth row, left shows 4-minute UV irradiation and right shows 5-minute UV irradiation.

(1) Preparation of Plate
Using an ozone/UV surface treatment apparatus, EKBIO-1100 (EBARA JITSUGYO CO., LTD.), 60 mm-diameter polystyrene cell-culture dishes (IWAKI) were irradiated with UV beams of 184.9 nm and 253.7 nm as follows: oxygen purge was performed at 25° C. for 5 minutes, and thereafter, UV was for one minute, 2 minutes, 3 minutes, 4 minutes or 5 minutes under humidification. A plate not irradiated with UV was used as a negative control. All plates having a surface treated with ozone/UV were coated with 5-fold diluted (×0.2) Matrigel (registered trade mark) (BD biosciences, #354277). The dish having a surface not treated with ozone/UV was used as positive control and coated with 5-fold diluted (×0.2), 2-fold diluted (×0.5) or undiluted Matrigel (registered trade mark). In this Example, 1 fold Matrigel (registered trade mark) refers to a coating obtained by dissolving 170 μl of Matrigel (registered trade mark) Growth factor reduced (Corning) in 10 ml of DMEM-F12 medium (Life Technologies) and applying the mixture to a culture-dish surface at normal temperature for one hour.
(2) Culture of Human iPS Cells
Human iPS cells (201B7) were seeded in Stem fit medium (AJINOMOTO) (Scientific Reports 4, Article number: 3594 (2014) doi: 10.1038/srep03594) (containing Y27364) on the polystyrene dishes prepared in the step (1) at $5.0 \times 10^4$ cells/dish and cultured at 37° C., 5% $CO_2$ under conditions of 100% humidity for 5 days. After culture, non-adherent cells were removed and the number of adherent cells was counted by ALP staining and ViCell and evaluated.
(3) Results
The results of the number of adherent cells after culture counted by ViCell are shown in FIG. 8. In the polystyrene dish not treated with ozone/UV, the number of adherent cells decreased as the concentration of Matrigel (registered trade mark) decreased. The number of the adherent cells on the surface treated with ozone/UV 1 to 2 minutes and coated with 5-fold diluted Matrigel (registered trade mark) (×0.2 concentration) was the same as that on the surface coated with 1 fold Matrigel (registered trade mark). It was suggesting that the number of adherent cells decreases as the time of ozone/UV treatment increases. The same tendency was confirmed by ALP staining (FIG. 9). Thus, it was demonstrated that the adhesion culture of human iPS cells can be achieved by applying an ozone/UV treatment for 1 to 2 minutes with the concentration of Matrigel (registered trade mark) reduced to ⅕ (0.2 fold).

(Example 11) Culture of Human iPS Cells on Plate Treated with Ozone-UV (Laminin Concentration)

Since it was demonstrated that human iPS cells efficiently adhere to a polystyrene dish having a surface treated with ozone/UV, at a low concentration of Matrigel (registered trade mark), whether the concentration of laminin, which is used similarly to Matrigel (registered trade mark), as a culture substrate for iPS cells, can be reduced or not, was investigated.
(1) Preparation of Plate
Using an ozone/UV surface treatment apparatus, EKBIO-1100 (EBARA JITSUGYO CO., LTD.), 60 mm-diameter polystyrene cell-culture dishes (IWAKI) were irradiated with UV of 184.9 nm and 253.7 nm as follows: oxygen purge was performed at 25° C. for 5 minutes, and thereafter, UV was applied one minute, 3 minutes or 5 minutes under humidification. A plate not irradiated with UV was used as a negative control. All plates having a surface treated with ozone/UV were coated with 5-fold diluted (×0.2) and 2-fold diluted (×0.5) laminin. The dish having a surface not treated with ozone/UV was used as a positive control and coated with 5-fold diluted (×0.2), 2-fold diluted (×0.5) or undiluted laminin 511E8. Note that, in the Example, 1-fold laminin refers to a coating obtained by diluting iMatrix (1 µg/µl) with PBS to obtain a final concentration of 0.5 ug/cm² and incubating at 37° C. in a 5% $CO_2$ incubator for one hour.

(2) Culture of Human iPS Cells

Human iPS cells (201B7) were seeded in Stem fit medium (AJINOMOTO) (Scientific Reports 4, Article number: 3594 (2014) doi: 10.1038/srep03594) (containing Y27364) on the polystyrene dishes prepared in the step (1) at $5.0 \times 10^4$ cells/dish and cultured at 37° C., 5% $CO_2$ under conditions of 100% humidity for 5 days. After culture, non-adherent cells were removed, and the number of adherent cells was counted by ALP staining and ViCell and evaluated.

(3) Results

Figure 10:
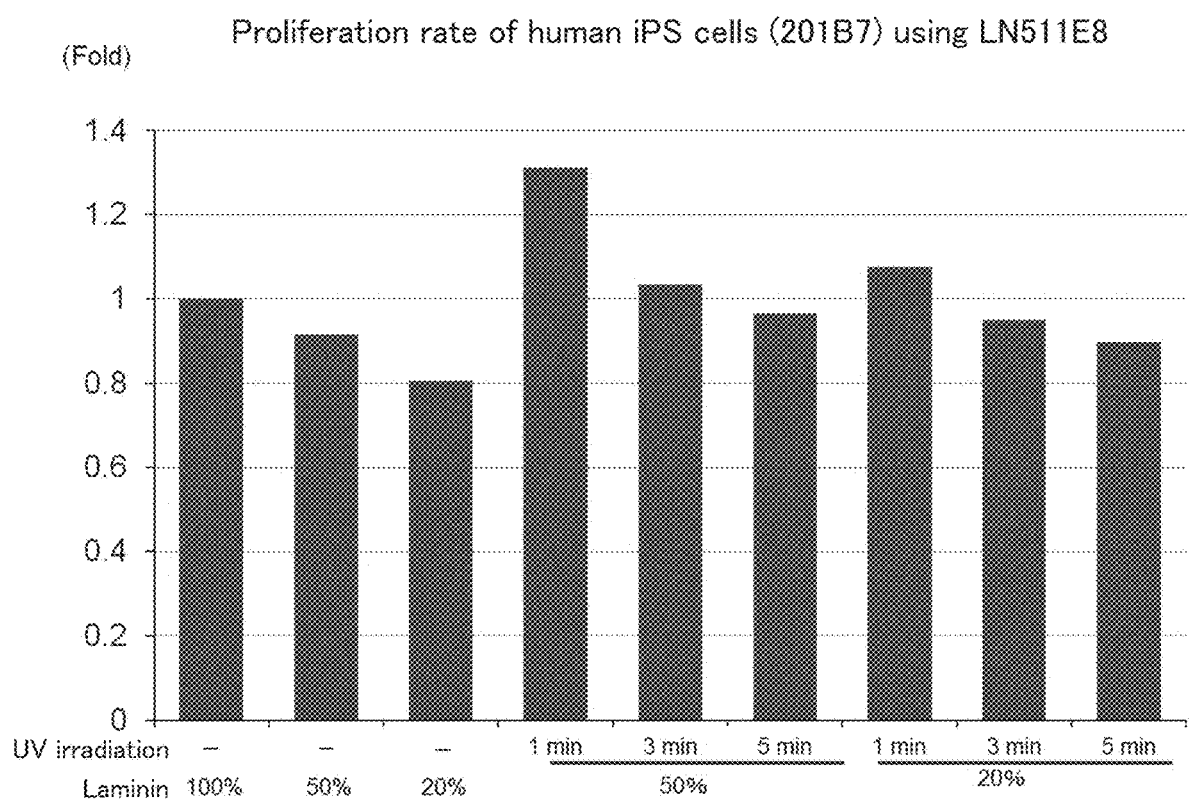
FIG. 10 shows graphs indicating the number of adherent cells after culturing human iPS cells (201B7) on polystyrene dishes in the presence of various concentration of laminin 511E8 for 3 days. The vertical axis represents the ratio (Fold) of the number of cultured cells to that cultured in the presence of 100% laminin 511E8 which is regarded as 1. Under the horizontal axis shows the time period (minutes) of ozone/UV treatment (UV irradiation) to a polystyrene dish (UV irradiation [min]) (upper-stage), and the percentage of concentration of laminin 511E8 used in culturing to the recommended concentration which is regarded as 100% (lower-stage). In the upper-stage under the horizontal axis, a bar (−) indicates no UV treatment.
Figure 11:
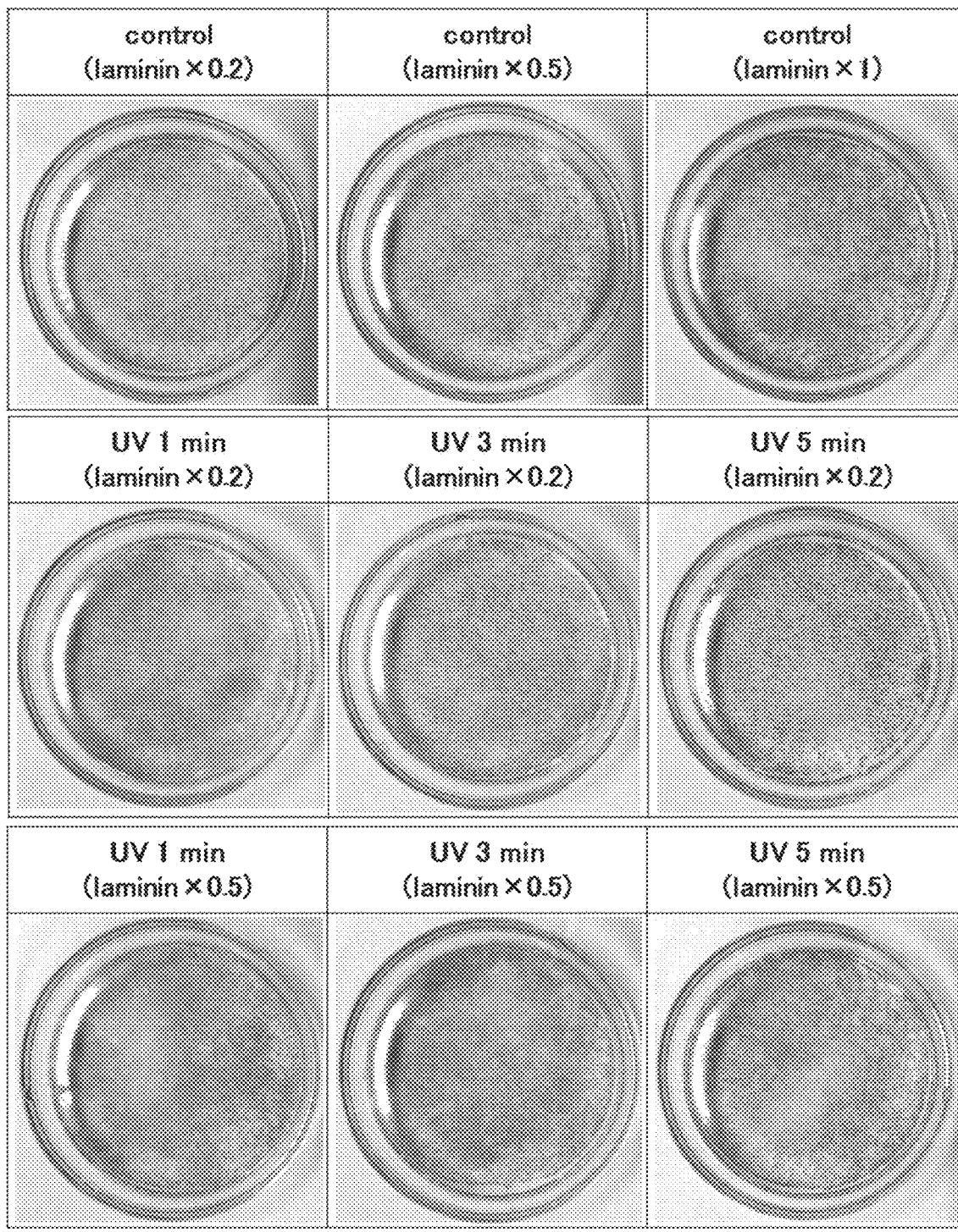
FIG. 11 shows pictures of adhered cells after culturing human iPS cells (201B7) on polystyrene dishes in the presence of various concentration of laminin for 5 days. The top pictures show the results of culturing on ozone/UV untreated dishes with laminin at concentrations of 0.2 fold, 0.5 fold, and 1 fold of the ordinary culture, from left to right. The middle pictures show the results of culturing on ozone/UV treated dishes with laminin at concentration of 0.2 fold of the ordinary culture, in which from left to right, UV was irradiated for 1 minute, 3 minutes and 5 minutes. The bottom pictures show the results of culturing on ozone/UV treated dishes with laminin at concentration of 0.5 fold of the ordinary culture, in which UV was irradiated for 1 minute, 3 minutes, and 5 minutes.

The results of the number of adherent cells after culture counted by ViCell are shown in FIG. 10. On the polystyrene dish not treated with ozone/UV, the number of adherent cells decreased as the concentration of laminin decreased. The number of the adherent cells on the surface treated with ozone/UV for 1 to 3 minutes with 2-fold diluted laminin (50% concentration) is more than those with 1-fold laminin. It was suggested that the number of adherent cells decreases as the time of ozone/UV treatment increases. Also, the number of the adherent cells on the surface treated with ozone/UV for one minute with 5-fold diluted laminin is more than those with 1-fold laminin. The results of the adherent cells after culture stained with ALP are shown in FIG. 11. On the polystyrene dishes not treated with ozone/UV, it was observed that the number of adherent cells tends to decrease as the concentration of laminin decreases (FIG. 11, upper stage). On the ozone/UV treated dish treated, the number of adherent cells is fewer than the control (1 fold concentration of laminin) at a 0.2-fold concentration of laminin, and the same number of adherent cells as 1-fold concentration of laminin was observed at 0.5-fold concentration of laminin on 1 to 3 minutes ozone/UV treated surface. Thus, it was demonstrated that human iPS cells can adhere and be cultured by applying an ozone/UV treatment for 1 to 3 minutes with reducing laminin concentration to ½ (0.5 fold).

(Example 12) Surface Analysis of Plate Treated with Ozone/UV (1) Preparation of Plate Cell-culture dishes (60 mm in diameter) made of polystyrene (No. 430589, Corning Incorporated, Massachusetts, USA) were irradiated with UV beams of 184.9 nm and 253.7 nm (as an ozone/UV surface modification treatment) by using an ozone/UV surface treatment apparatus, EKBIO-1100 (EBARA JITSUGYO CO., LTD.) follows: oxygen purge was performed at 40° C. for 5 minutes, and thereafter UV was applied for one minute, 3 minutes, 5 minutes, 10 minutes or 20 minutes in humidification conditions. As a control (Control), a 60 mm-diameter polystyrene dish (No. 430589, Corning Incorporated, Massachusetts, USA) not treated with UV was used.

(2) Surface Analysis

Each of the dishes, plates of 15 mm-squares were cut out and subjected to surface analysis using a time-of-flight secondary ion mass spectrometer (Ulvac-Phi Inc., PHI nano-TOF II). The primary ion beam for analysis was 30 kV $Bi_3^{++}$ 6.0 to 7.0 nA DC. The scanning range was within 500×500 µm (number of pixels: 256×256 µm, display range 128×128 µm). The path width and frame-number of the primary ion beam were 12 n-seconds and 64 to 75 times ($1 \times 10^{11}$ frames/cm²). The charge neutralization was set at 10 eV electron beam+10 eV A⁺. Since the ions that can be generated from a polystyrene are all cations, a positive ion molecular weight spectrum alone was detected.

(3) Results

The results are shown in FIGS. 10A to C. The surface molecules were classified into an adhesion promoting factor group and an adhesion inhibitory factor group in accordance with Jing Yang, et al. Biomaterials, 31: 8827-8838, (2010) and evaluated. More specifically, among the molecules generated from a polystyrene, $C_3H_7^+$ (molecular weight 43.0554), $C_5H_7^+$ (molecular weight 67.0556), and $C_7H_5O^+$ (molecular weight 105.0317) were analyzed as adhesion promoting factors; and $C_3H_5^+$ (molecular weight 41.0395), $C_2H_3O^+$ (molecular weight 43.0191), $C_3H_5O^+$ (molecular weight 57.0347), $C_3H_7O^+$ (molecular weight 59.0498) and $C_6H_5^+$ (molecular weight 77.0364) were analyzed as adhesion inhibitory factors. $C_3H_7^+$. (molecular weight 43.0554) and $C_2H_3O^+$ (molecular weight 43.0191) were identified by confirming the presence/absence of O. As the result of surface analysis, particularly $C_7H_5O^+$ (molecular weight: about 105), which showed a marked change, was determined as a representative adhesion promotion factor increased by an ozone/UV surface modification treatment, and $C_2H_3O^+$ (molecular weight: about 43) was determined as a representative adhesion inhibitory factor increased by an ozone/UV surface modification treatment. The UV irradiation time period and a change of these molecules were analyzed. $C_7H_5O^+$ (molecular weight: about 105) is conceivably a substance represented by the following chemical formula (a); and $C_2H_3O^+$ (molecular weight: about 43) is a substance represented by the following chemical formula (c).

Specifically, the ratios of these factors in the molecules constituting a dish surface, were calculated in accordance with the respective expressions: (ratio of adhesion promotion factor)=(expression level of adhesion promotion factor)/{(expression level of all factors)−(expression level of an external factor)}, and (ratio of adhesion inhibitory factor)= (expression level of adhesion inhibitory factor)/{(expression level of all factors)−(expression level of an external factor)}. Based on these, a change in each of the ratios of these factors with the UV irradiation time was confirmed (FIG. 11). The "external factor" is an external factor serving as a contamination factor which possibly attaches during an ozone/UV treatment and during cutting-out of dishes; and more specifically include Na⁺ (molecular weight 22.9932), $(CH_3)_3Si^+$ (molecular weight 73.0518) and $(CH_3)_3Si—O—Si (CH_3)_2^+$. As a result, $C_7H_5O^+$ started increasing from one minute after UV irradiation and reached a maximum at 3 minutes, whereas $C_2H_3O^+$ gradually started increasing from 3 minutes after UV irradiation and was found to constantly increase up to 20 minutes after UV irradiation.

Figure 12A:
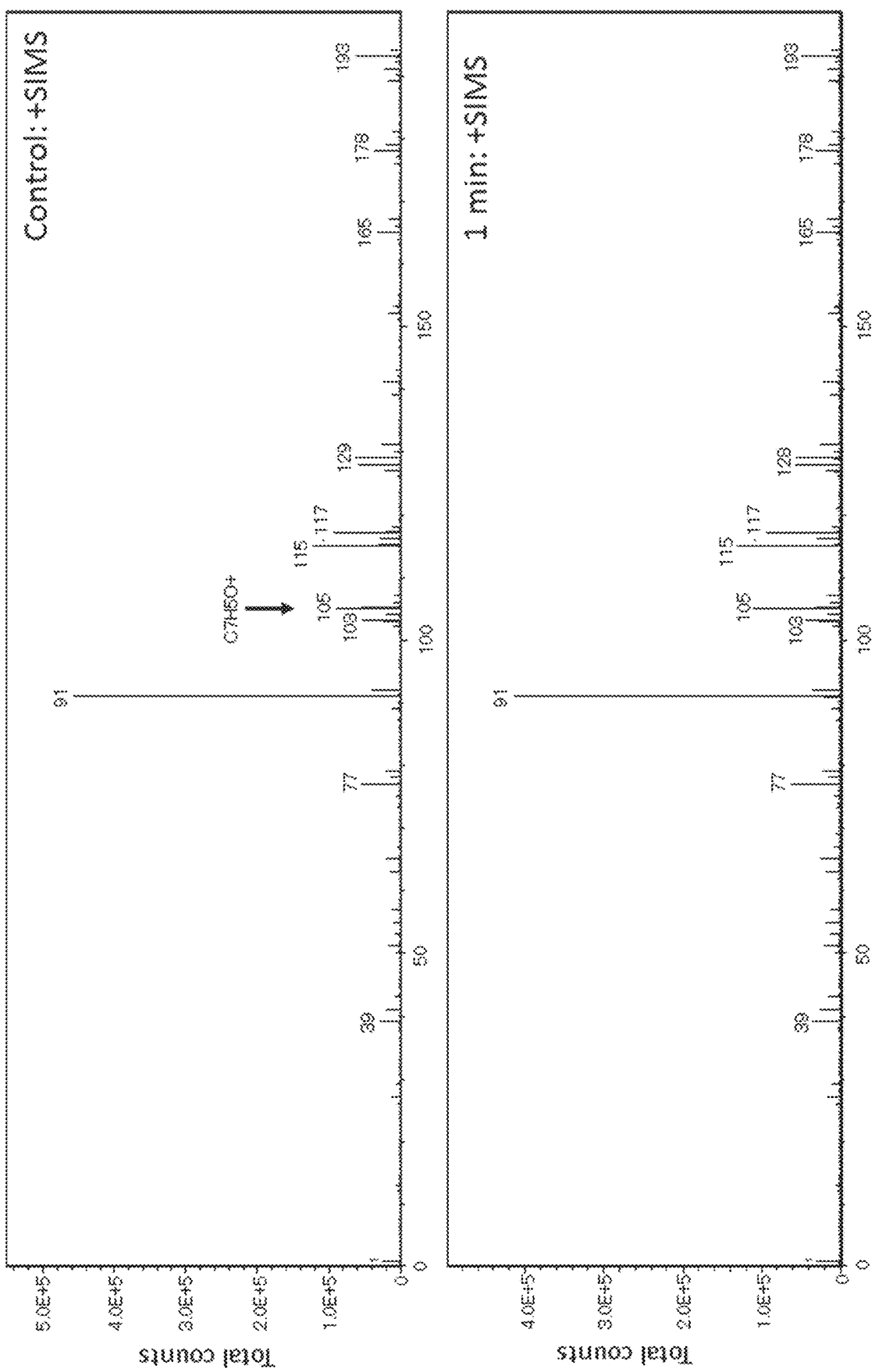
FIG. 12A shows a graph showing the results of analysis of the surface of a UV untreated polystyrene dish (control) and the surface of a polystyrene dish treated with ozone/UV for one minute (1 min) by a time-of-flight secondary ion mass spectrometer (Ulvac-Phi Inc., PHI nanoTOF II). The vertical axis represents the count number and the horizontal axis represents mass-to-charge ratio (m/z).
Figure 13:
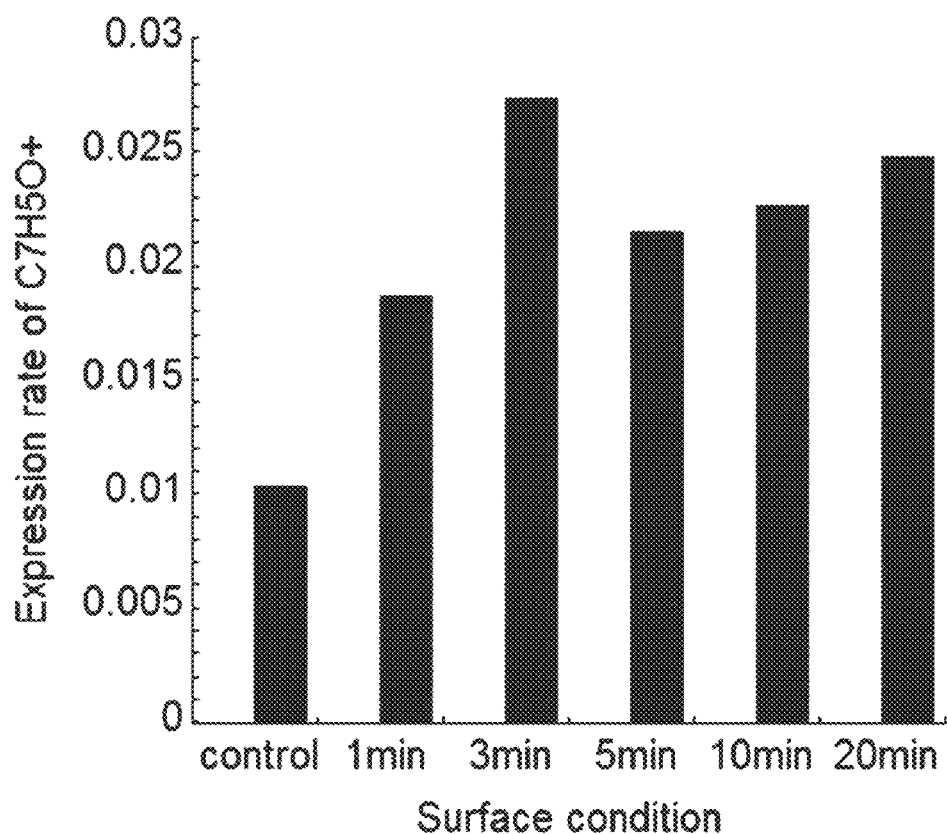
FIG. 13 is a graph showing the results of analysis of the ozone/UV treated surfaces by a time-of-flight secondary ion mass spectrometer (Ulvac-Phi Inc., PHI nanoTOF II). The vertical axis shows ratio of generated amount of $C_7H_5O^+$ to that of all molecules. The horizontal axis represents UV irradiation time (minutes).
Figure 14:
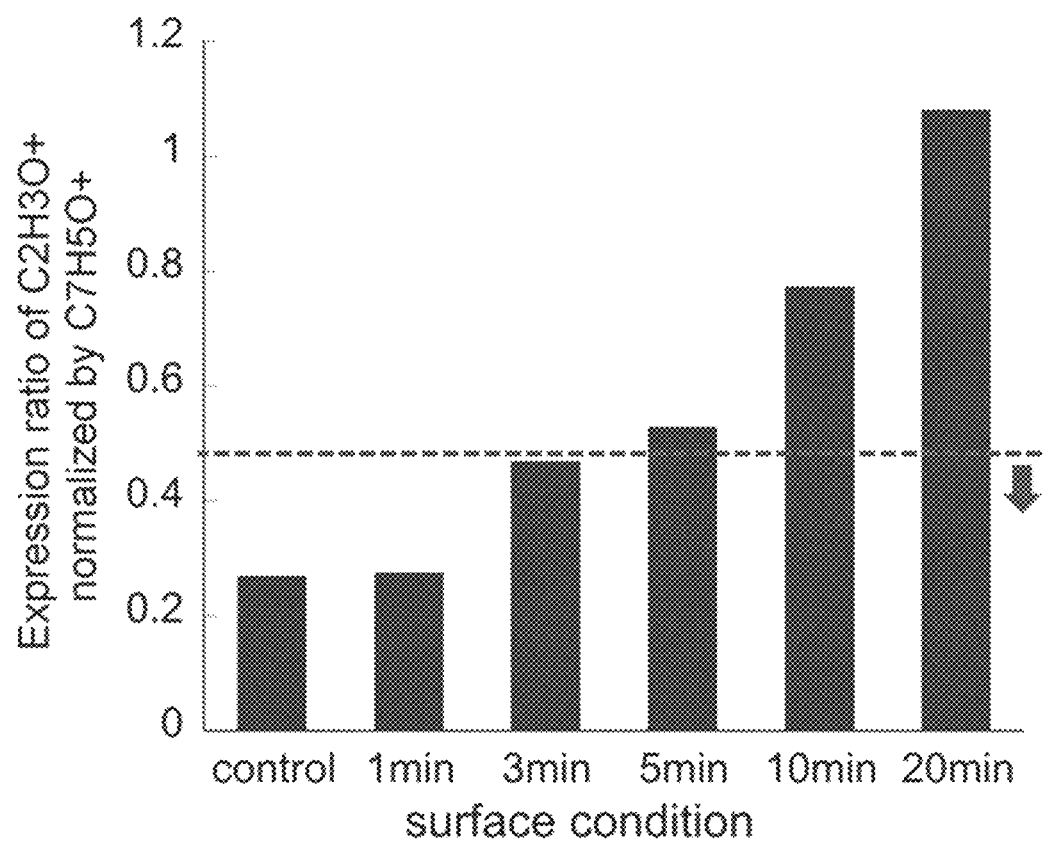
FIG. 14 is a graph showing the result of analysis of the ozone/UV treated surfaces by a time-of-flight secondary ion mass spectrometer (Ulvac-Phi Inc., PHI nanoTOF II). The vertical axis shows the proportion of the ratio of the $C_2H_3O^+$ molecules to all molecules to the ratio of the $C_7H_5O^+$ molecules to all molecules. The horizontal axis represents UV irradiation time (minutes).
Figure 15:
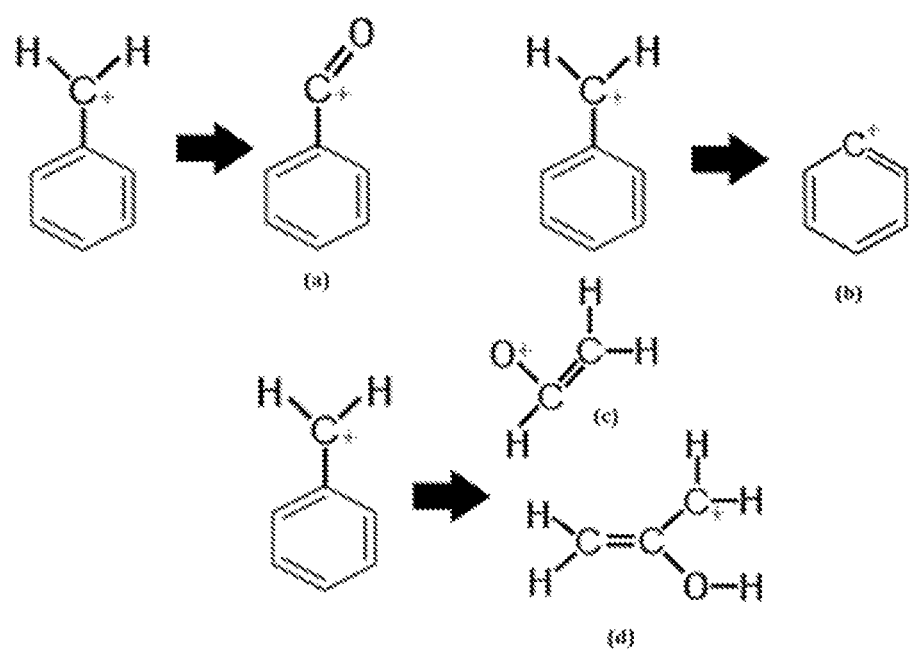
FIG. 15 illustrates the chemical formulas of surface molecules produced from polystyrene.

In the experimental results of iPS cells, the UV irradiation time for attaining the same number of adherent cells as in the dish coated with Matrigel (registered trade mark) of a concentration (1 fold) presently used in iPS culture was 1 to 3 minutes. Accordingly, in the case where the $C_7H_5O^+$ ratio in a dish surface is 0.015 or more, the number of adherent cells is the same or more as that obtained in 1 fold Matrigel (registered trade mark) coating dish. Furthermore, $C_7H_5O^+$ in the dish surface reached a maximum at UV irradiation time of 3 minutes, and then once decreased at 5 minutes and thereafter tended to increase from 5 to 20 minutes. In contrast, the number of the adherent cells reached a maximum at a UV irradiation time of 1 to 3 minutes and thereafter decreased. Then, the adhesion inhibitory factor other than the adhesion promotion factor was also investigated. As a result, $C_2H_3O^+$ sharply increased after UV was irradiated for 5 minutes. The ratio of (ratio of adhesion inhibitory factor)/(ratio of adhesion promotion factor) was calculated (FIG. 12). As a result, it was found that if the ratio is 0.485 or less, the number of adherent cells increases.

The invention claimed is:

1. A method for producing a substrate for supporting cells having a cell supporting surface, comprising:

humidifying the periphery of a polystyrene based substrate, and irradiating Ultra Violet (UV) to the cell supporting surface of the polystyrene based substrate under (i) an oxygen atmosphere, (ii) an ozone atmosphere, or (iii) an oxygen atmosphere and an ozone atmosphere, wherein said irradiation is conducted (i) during said humidification, (ii) after said humidification, or (iii) during and after said humidification, wherein a ratio of $C_7H_5O^+$ to all molecules generated in the polystyrene by UV irradiation by TOF-SIMS (time-of-flight secondary ion mass spectrometer) is 0.015 or more, and wherein a ratio between $C_7H_5O^+$ to all molecules and a ratio of $C_2H_3O^+$ to all molecules generated in the polystyrene by UV irradiation by TOF-SIMS is 0.485.

2. The method for producing a substrate for supporting cells of claim 1, wherein the UV irradiation is performed by applying UV beams with wavelength of 184.9 nm and 253.7 nm in average.

3. The method for producing a substrate for supporting cells of claim 1, wherein the UV irradiation is performed until a water contact angle of a surface of the non-fluorine resin becomes between 40 and 70°.

4. The method for producing a substrate for supporting cells of claim 1, wherein the UV irradiation is performed for 1 to 3 minutes.

5. The method of claim 1, wherein UV having wavelength of 184.9 and 253.7 nm are irradiated from two 6 Watt (W) ozone generation lamps.

6. The method of claim 1, wherein the distance from UV lamps to the substrate is 3 to 5 cm.

7. The method of claim 1, wherein the cell supporting surface was caused a chemical shift of (i) C—C bond, (ii) C—H bond, or (iii) C—C bond and C—H bond.

8. The method of claim 1, wherein the cell supporting surface has an extremely low amount of carboxy groups compared to a substrate treated with UV/ozone under the same conditions but non-humidification.

9. The method of claim 1, wherein the cell supporting surface has a water contact angle of 40 to 70°.

10. The method of claim 1, wherein the cell supporting surface enables stem cells to adhere or proliferate on the surface with maintaining an undifferentiated state in the absence of feeder cells.

11. The method of claim 1, wherein stem cells adhere or proliferate on the supporting surface coated with Matrigel (registered trade mark) at 0.2 fold concentration of that required for adhesion of the stem cells onto a non-treated surface of the polystyrene based substrate.

12. The method of claim 1, wherein stem cells adhere or proliferate on the supporting surface coated with laminin at 0.2 fold concentration of that required for adhesion of the stem cells onto a non-treated surface of the polystyrene based substrate.

13. The method of claim 11, wherein the stem cells are mouse iPS cells or human iPS cells.

14. The method of claim 1, wherein the substrate is an adherent cell culturing container.

15. The method of claim 14, wherein the adherent cell culturing container is a dish for adherent cell culture.

\* \* \* \* \*